(12) United States Patent
Satou et al.

(10) Patent No.: US 8,334,129 B2
(45) Date of Patent: Dec. 18, 2012

(54) MICROORGANISM CAPABLE OF PRODUCING POLYHYDROXYALKANOATE, POLYHYDROXYALKANOATE SYNTHASE, AND GENE ENCODING THE SAME

(75) Inventors: Yasuharu Satou, Sapporo (JP); Kenji Tajima, Sapporo (JP); Masanobu Munekata, Sapporo (JP); Tokuo Matsushima, Sapporo (JP)

(73) Assignee: Hitachi Chemical Co., Ltd., Tokyo (JP)

( * ) Notice: Subject to any disclaimer, the term of this patent is extended or adjusted under 35 U.S.C. 154(b) by 549 days.

(21) Appl. No.: 12/459,941

(22) Filed: Jul. 9, 2009

(65) Prior Publication Data
US 2010/0035313 A1 Feb. 11, 2010

(30) Foreign Application Priority Data

Jul. 10, 2008 (JP) ................. 2008-180132

(51) Int. Cl.
*C12N 1/20* (2006.01)
*C12P 7/64* (2006.01)
*C12P 21/00* (2006.01)
*C12Q 1/48* (2006.01)
*C12N 9/10* (2006.01)

(52) U.S. Cl. ....... 435/253.3; 435/193; 435/15; 435/135; 435/71.2

(58) Field of Classification Search ................ 435/252.1, 435/254.1, 253
See application file for complete search history.

(56) References Cited

FOREIGN PATENT DOCUMENTS

| | | | |
|---|---|---|---|
| JP | S63-248394 A | 10/1988 | |
| JP | 2001-178484 | 7/2001 | |
| JP | 2002-335966 | 11/2002 | |
| JP | 2004-321167 | 11/2004 | |
| JP | 2006-320256 | 11/2006 | |

OTHER PUBLICATIONS

Stackebrandt, E., Encyclopedia of Life Sciences, pp. 1-7, 2001.*
Alexander Steinbuchel et al., "Diversity of bacterial polyhydroxyalkanoic acids", FEMS Microbiology Letters of 1995, pp. 128-219 to 128-228.
"*Pseudomonas thermotolerans* sp. nov., . . . " by Cella M. Manaia et al. in International Journal of Systematic and Evolutionary Microbiology, in 2003, vol. 52, pp. 2203-2209.
"Polyhydroxyalkanoate synthases PhaC1 and PhaC2 . . . " by Jing-Yu Chen, et al. in FEMS Microbiology Letters, in 2004, vol. 234, pp. 231-237.

* cited by examiner

*Primary Examiner* — Delia Ramirez
(74) *Attorney, Agent, or Firm* — RatnerPrestia

(57) ABSTRACT

Problem to be Solved: To provide a new microorganism capable of producing a polyhydroxyalkanoate (PHA), a PHA synthase gene, an expression cassette including the gene, a vector including the expression cassette, a transformant transformed by the vector, a polypeptide having PHA synthase activity, a method for producing a PHA synthase and a method for producing a PHA.

Solution: The new microorganism is capable of producing a polyhydroxyalkanoate comprising a 16S rRNA gene whose polynucleotide sequence shows 99% or more homology to a polynucleotide sequence represented by SEQ ID No: 1, having an optimum temperature of an activity temperature range for the growth and PHA production of the microorganism of at least 45° C. and being capable of growing at a pH range from 6 to 10.

3 Claims, 13 Drawing Sheets

Fig.1

| Temperature | Carbon source | Dry microbial cell body volume (g/L) | PHA production volume (g/L) | PHA content in the dry microbial cell body (wt%) | Molecular weight | | |
|---|---|---|---|---|---|---|---|
| | | | | | Mn | Mw | Mn/Mw |
| 45°C | Sodium dodecanoate | 0.302 | 0.109 | 36.1 | 76,690 | 169,175 | 2.21 |
| | Sodium octanoate | 1.797 | 0.503 | 28.0 | 107,026 | 260,021 | 2.43 |
| | Sodium acetate | 0.565 | 0.057 | 10.1 | 73,373 | 158,459 | 2.16 |
| | Neutralized BDFB (1st culturing) | 1.500 | 0.609 | 40.6 | 35,692 | 69,421 | 1.95 |
| | Neutralized BDFB (2nd culturing) | 1.294 | 0.366 | 28.3 | 40,243 | 76,252 | 1.89 |
| 30°C | Neutralized BDFB | 0.618 | — | — | — | — | — |
| 37°C | Neutralized BDFB | 1.055 | — | — | — | — | — |

Fig.2

| Temperature | Carbon source | PHA production volume (g/L) | PHA content in the dry microbial cell body (wt%) | PHA composition (%) | | | | | |
|---|---|---|---|---|---|---|---|---|---|
| | | | | 3HB (C4) | 3HHx (C6) | 3HO (C8) | 3HD (C10) | 3HDD (C12) |
| 45°C | Sodium dodecanoate | — | — | 0.7 | 6.3 | 40.2 | 37.8 | 15.0 |
| | Sodium octanoate | — | — | 0.9 | 10.7 | 82.5 | 5.7 | 0.1 |
| | Sodium acetate | — | — | 1.0 | 1.4 | 10.4 | 84.4 | 2.9 |
| | Neutralized BDFB (1st culturing) | — | — | 0.8 | 5.7 | 25.1 | 59.8 | 8.6 |
| | Neutralized BDFB (2nd culturing) | — | — | 0.8 | 6.1 | 25.4 | 60.6 | 7.2 |
| 30°C | Neutralized BDFB | 0.080 | 12.9 | 0.7 | 10.5 | 32.0 | 46.8 | 10.1 |
| 37°C | Neutralized BDFB | 0.117 | 11.1 | 0.0 | 7.3 | 29.9 | 53.6 | 9.3 |

US 8,334,129 B2

MICROORGANISM CAPABLE OF PRODUCING POLYHYDROXYALKANOATE, POLYHYDROXYALKANOATE SYNTHASE, AND GENE ENCODING THE SAME

TECHNICAL FIELD

The present invention generally relates to a new microorganism capable of producing a polyhydroxyalkanoate (PHA), a PHA synthase gene, an expression cassette including the gene, a vector including the expression cassette, a transformant transformed by the vector, a polypeptide having PHA synthase activity, a method for producing a PHA synthase and a method for producing a PHA.

BACKGROUND OF THE ART

Currently, some polymers, such as synthetic plastics derived from fossil fuels (e.g. petroleum), are unable to be degraded. So, the polymers are accumulated semipermanently in natural environment, resulting in various environmental problems. Amid growing public concerns over recent environmental problems, new polymers are being developed from recyclable sources that are not derived from fossil fuels.

Under these circumstances, much academic attention has been focused on polyhydroxyalkanoate (PHA), which is produced from reproducible biological organic resources (biomass) such as sugar and vegetable oil by fermentation method, as a biodegradable plastic (Green Plastics, known as eco-friendly polymer) having thermoplasticity and excellent bio-degradable and biocompatible properties. Such biodegradable plastics are currently developed in technical properties toward practical use, and are expected to become leading biomaterials in biological and medical fields.

PHA is conventionally known as a polyester-type organic molecule polymer that can be accumulated in a microbial cell body in many types of microorganisms, as disclosed in Japanese Unexamined Patent Application Publication No. 2006-320256 (a microorganism capable of producing polyhydroxybutyrate (PHB) that belongs to genus Methylocystis that can accumulate PHB in a microbial cell body).

Meanwhile, a PHA that is produced by a microorganism and accumulated in a microbial cell body thereof is found to include 90 types or more of monomer structures (see FEMS Microbiol. Lett., 1995, 128219 to 128228). In PHA, properties are significantly affected by its constituting monomer units, like 3-hydroxybutyrate (3HB), from which a typical PHA is produced by a microorganism. However, such a PHA is of high crystallinity and low flexibility, resulting in limited industrial uses.

In order to obtain a PHA having monomer units other than 3-hydroxybutyrate (3HB), the following operations are required: changes in the type of PHA-producing microorganism, culture medium composition and culture conditions, and the isolation of microorganism and use of transformants transformed by gene recombinant techniques. For example, Japanese Unexamined Patent Application Publication No. 2001-178484 discloses a method for producing a PHA including at least one of 6 numbers of carbon atoms (hereinafter called C6), C8, C10, C12 and C14 monomer units in *Pseudomonas cichorii* YN2 cultured in a culture medium, by assimilating acetic acid or its salt as a sole carbon source. Another Japanese Unexamined Patent Application Publication No. 2004-321167 discloses a method for producing a PHA comprising C6 to C10 monomer units by culturing a specific transformant in a culture medium including C6 to C10 as carbon sources.

A ratio of monomer units in a PHA varies according to substrate specificity of PHA synthase and monomer synthetic pathway in a host. PHA synthases are classified into four groups (types I to IV) according to primary structure and substrate specificity. Type I and III PHA synthases show substrate specificity in a hydroxyacyl-CoA of short-chain length (about C3 to 6), type II PHA synthase shows substrate specificity in a hydroxyacyl-CoA of medium-chain length (about C6 to 12), and Type IV PHA synthase shows substrate specificity in a hydroxyl-CoA of short to medium-chain length (about C4 to 8). Due to a dependence of properties on monomer composition in PHA, the production of versatile PHA requires PHA synthase having various substrate specificities.

Meanwhile, Japanese Unexamined Patent Application Publication No. 2002-335966 discloses a strain that produces poly-3-hydroxybutyrate at about medium temperature (40 to 50° C.) and belongs to *bacillus* (bacilliform bacterium) sp., a PHA synthase, a gene encoding the same, etc. By culturing the strain or using the PHA synthase obtained, a PHA with high thermal stability can be stably produced even at about medium temperature.

DISCLOSURE OF THE INVENTION

Problem to be Solved

However, the above-cited documents are unable to disclose microorganisms that can produce a PHA having units other than 3HB units as the main constituent at about medium temperature, and PHA synthase.

It is, therefore, one object of the present invention to provide a new microorganism capable of producing a PHA, a PHA synthase gene, an expression cassette including the gene, a vector including the expression cassette, a transformant transformed by the vector, a polypeptide having PHA synthase activity, a method for producing a PHA synthase and a method for producing a PHA.

Means for Solving the Problem

The following items, respectively alone or in combination, contribute further to solve the object:

(1) A new microorganism being capable of producing a polyhydroxyalkanoate and comprising a 16S rRNA gene (16S rDNA) whose polynucleotide sequence shows 99% or more homology to a polynucleotide sequence represented by SEQ ID No: 1, comprising the following characteristics (a) and (b):
  (a) having an optimum temperature of an activity temperature range for the growth and PHA production of said microorganism of at least 45° C.;
  (b) being capable of growing at a pH range from 6 to 10.

(2) The microorganism according item (1), furthermore comprising the following characteristics (c) and/or (d):
  (c) being an aerobic Gram-negative polar flagellate *bacillus* (bacilliform bacterium) being tolerant of catalase, oxidase, arginine dihydrolase in 4% NaCl at 37° C. and 4% NaCl at 50° C.;
  (d) capable of assimilating sodium citrate, sodium pyruvate, sodium succinate, sodium acetate, sodium propionate, sodium caproate, sodium malate, betaine, L-lysine, L-asparagine, L-serine, L-glutamine, L-alanine, L-isoleucine, L-proline, dodecane, tridecane, hexadecane, nonadecane, eicosane, palmitic acid, octanal, 1-octanol, lauryl alcohol, Tween 80 and sodium benzoate; preferably, said microorganism comprises both characteristics (c) and (d).

(3) A new microorganism being capable of producing polyhydroxyalkanoate and being *Pseudomonas* sp. SG4502 (NITE BP-578).

(4) A PHA synthase I gene which encodes a polypeptide having at least one of the following characteristics (a), (b) and (c):
- (a) a polypeptide comprising an amino acid sequence represented by SEQ ID No: 3;
- (b) a polypeptide having PHA synthase activity, and comprising an amino acid sequence, in which one or more amino acids are deleted, substituted, inserted and/or added in said polypeptide comprising an amino acid sequence represented by SEQ ID No: 3;
- (c) a polypeptide having at least 80% or more of amino acid sequence identity with respect to said polypeptide comprising an amino acid sequence represented by SEQ ID No: 3 and PHA synthase activity.

(5) A PHA synthase I gene which comprises a polynucleotide sequence having at least one of the following characteristics (a), (b), (c) and (d):
- (a) A polynucleotide sequence represented by SEQ ID No: 2;
- (b) a polynucleotide sequence that hybridizes with said polynucleotide sequence represented by SEQ ID No: 2 or its complementary polynucleotide sequence under a stringent condition and encodes a protein having PHA synthase activity;
- (c) a polynucleotide sequence, in which one or more polynucleotide sequences are deleted, substituted, inserted and/or added in said polynucleotide sequence represented by SEQ ID No: 2, encoding a protein having PHA synthase activity;
- (d) a polynucleotide sequence encoding a protein having at least 80% or more of polynucleotide sequence identity with respect to said polynucleotide sequence represented by SEQ ID No: 2 and PHA synthase activity.

(6) A PHA synthase II gene which encodes a polypeptide having at least one of the following characteristics (a), (b) and (c):
- (a) a polypeptide comprising an amino acid sequence represented by SEQ ID No: 5;
- (b) a polypeptide having PHA synthase activity, and comprising an amino acid sequence, in which one or more amino acids are deleted, substituted, inserted and/or added in said polypeptide comprising an amino acid sequence represented by SEQ ID No: 5;
- (c) a polypeptide having at least 80% or more of amino acid sequence identity with respect to said polypeptide comprising an amino acid sequence represented by SEQ ID No: 5 and PHA synthase activity.

(7) A PHA synthase II gene which comprises a polynucleotide sequence having at least one of the following characteristics (a), (b), (c) and (d):
- (a) a polynucleotide sequence represented by SEQ ID No: 4;
- (b) a polynucleotide sequence that hybridizes with said polynucleotide sequence represented by SEQ ID No: 4 or its complementary polynucleotide sequence under a stringent condition and encodes a protein having PHA synthase activity;
- (c) a polynucleotide sequence, in which one or more polynucleotide sequences are deleted, substituted, inserted and/or added in said polynucleotide sequence represented by SEQ ID No: 4, encoding a protein having PHA synthase activity;
- (d) a polynucleotide sequence encoding a protein having at least 80% or more of polynucleotide sequence identity with respect to said polynucleotide sequence represented by SEQ ID No: 4 and PHA synthase activity.

(8) A gene expression cassette comprising the PHA synthase I gene according to item (4) or (5), the PHA synthase II gene according to item (6) or (7), and one or more genes selected from the group consisting of genes of polyhydroxyalkanoate-degrading enzymes, wherein PHA-degrading enzyme encodes a polypeptide having at least one of the following characteristics (a), (b) and (c):
- (a) a polypeptide comprising an amino acid sequence represented by SEQ ID No: 7;
- (b) a polypeptide having PHA degrading activity and comprising an amino acid sequence, in which one or more amino acids are deleted, substituted, inserted and/or added in said polypeptide comprising an amino acid sequence represented by SEQ ID No: 7;
- (c) a polypeptide having at least 80% or more of amino acid sequence identity with respect to said polypeptide comprising an amino acid sequence represented by SEQ ID No: 7 and PHA degrading activity.

(9) A gene expression cassette comprising the PHA synthase I according to item (4) or (5), the PHA synthase II gene according to item (6) or (7), and one or more genes selected from the group consisting of genes of polyhydroxyalkanoate-degrading enzymes, wherein PHA-degrading enzyme comprises a polynucleotide sequence at least one of the following (a), (b), (c) and (d):
- (a) a polynucleotide sequence represented by SEQ ID No: 6;
- (b) a polynucleotide sequence that hybridizes with said polynucleotide sequence represented by SEQ ID No: 6 or its complementary polynucleotide sequence under a stringent condition and encodes a protein having PHA synthase activity;
- (c) a polynucleotide sequence, in which one or more polynucleotide sequences are deleted, substituted, inserted and/or added in said polynucleotide sequence represented by SEQ ID No: 6, encoding a protein having PHA synthase activity;
- (d) a polynucleotide sequence encoding a protein having at least 80% or more of polynucleotide sequence identity with respect to said polynucleotide sequences represented by SEQ ID No: 6 and PHA synthase activity.

(10) A vector comprising the gene expression cassette of this invention.

(11) A vector being a recombinant plasmid of pC1ZC2_SG4502 (NITE BP-579).

(12) A transformant transformed by the vector according to item (10) or (11).

(13) The transformant according to item (12) being *Escherichia coli.*

(14) A peptide having at least one of the following characteristics (a), (b), (c), (d), (e) and (f).
- (a) being a polypeptide comprising an amino acid sequence represented by SEQ ID No: 3;
- (b) being a polypeptide having PHA synthase activity and comprising an amino acid sequence, in which one or more amino acids are deleted, substituted, inserted and/ or added in said polypeptide comprising an amino acid sequence represented by SEQ ID No: 3;
- (c) being a polypeptide having at least 80% or more of amino acid sequence identity with respect to said polypeptide comprising an amino acid sequence represented by SEQ ID No: 3 and PHA synthase activity;

(d) being a polypeptide comprising an amino acid sequence represented by SEQ ID No: 5;

(e) being a polypeptide having PHA synthase activity and comprising an amino acid sequence, in which one or more amino acids are deleted, substituted, inserted and/or added in said polypeptide comprising an amino acid sequence represented by SEQ ID No: 5;

(f) being a polypeptide having at least 80% of amino acid sequence identity with respect to said polypeptide comprising an amino acid sequence represented by SEQ ID No: 5 and PHA synthase activity.

(15) A method for producing a polyhydroxyalkanoate synthase to collect a polyhydroxyalkanoate synthase from a culture obtained by culturing the microorganism according to any one of items (1) to (3) or said transformant according to item (12) or (13).

(16) A method for producing a polyhydroxyalkanoate to collect a polyhydroxyalkanoate from a culture obtained by culturing the microorganism according to any one of items (1) to (3) or the transformant according to item (12) or (13) (or in vivo PHA production method).

(17) A method for producing a polyhydroxyalkanoate to produce a polyhydroxyalkanoate using a polyhydroxyalkanoate synthase obtained by the method for producing a polyhydroxyalkanoate synthase according to item (15) (or in vitro PHA production method).

(18) The method according to item (17), wherein a poly-3-hydroxyalkanoate is produced using a α-unsaturated fatty acid as a substrate. Preferably, said α-unsaturated fatty acid is 2-hexenoic acid for producing poly-3-hydroxyhexanoate, and crotonic acid for producing poly-3-hydroxybutyrate.

(19) A use of a polyhydroxyalkanoate (PHA) synthase according to item (14) or a microorganism according to any one of items (1) to (3) for producing polyhydroxyalkanoate (PHA).

Accordingly, this invention provides a microorganism capable of producing a PHA, a PHA synthase gene derived from said microorganism, an expression cassette comprising the gene, a vector comprising the expression cassette, a transformant transformed by the vector, a polypeptide having PHA synthase activity. This invention also provides a PHA synthase derived from the new microorganism and a PHA produced by said PHA synthase. Furthermore, this invention provides a use of said PHA synthase or said microorganism for producing PHA.

BRIEF DESCRIPTION OF THE DRAWINGS

The above and other objects of the invention will be seen by reference to the description taken in connection with the drawings, in which:

FIG. 1 is a table showing PHA production volume from SG4502 and molecular weight in Example 2;

FIG. 2 is a table showing PHA composition from SG4502 in Example 2;

BEST MODE FOR CARRYING OUT THE INVENTION

Figure 3:
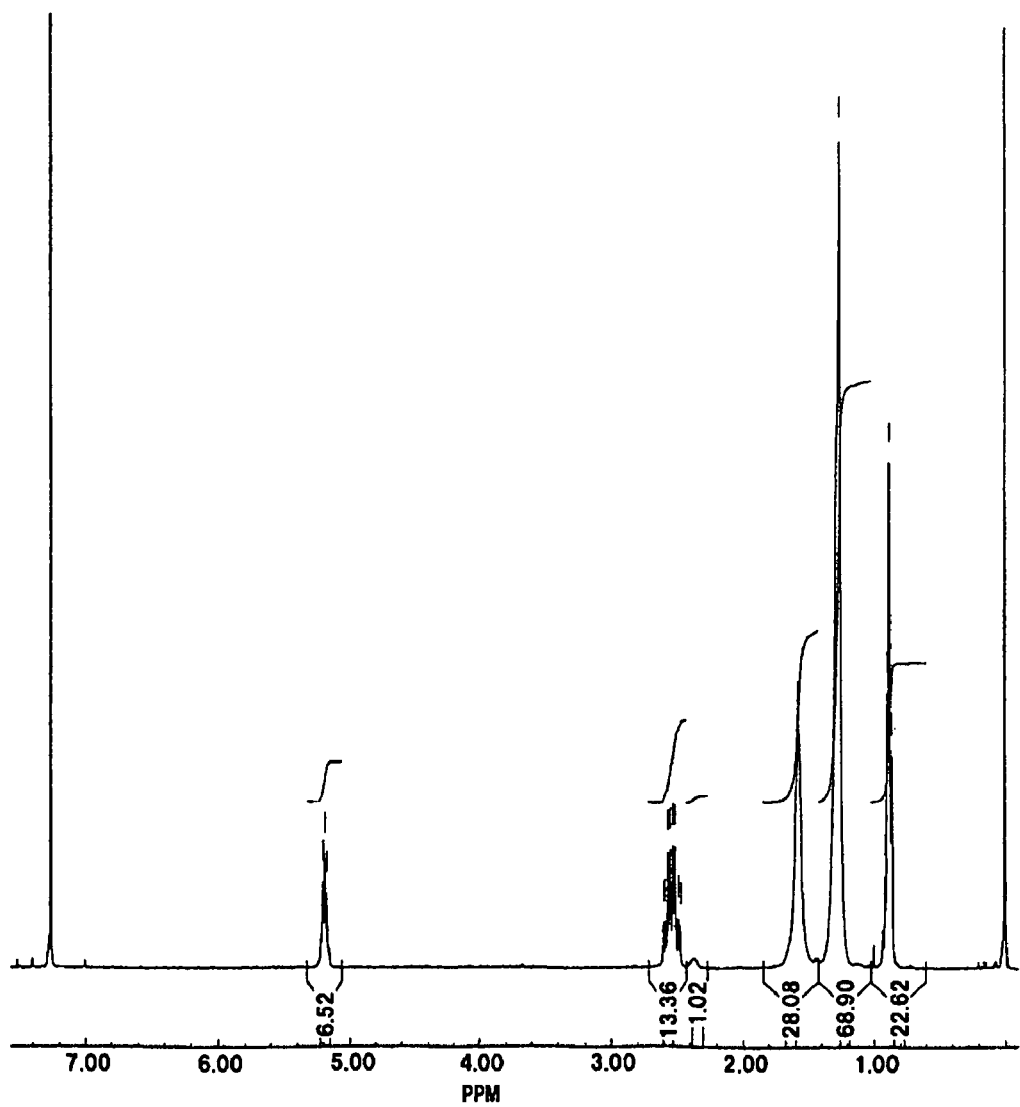
FIG. 3 is a diagram showing $^1$H-NMR spectrum of a compound produced by SG4502 in Example 2 (2), using sodium dodecanoate as a carbon source.

The present invention will be described in detail in the following description. A PHA produced by this invention is exemplified comprising at least hydroxyalkanoate (HA) as a monomer unit, as shown in the following formula [1].

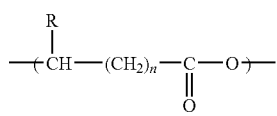

[Formula 1]

(R is a hydrocarbon having 0, 1 or more C, and N is an Integer of 0, 1 or More.)

An HA, as a monomer unit of PHA produced by this invention, can be, for example, lactic acid (2-hydroxy propionate; LA), glycolic acid, 3-hydroxy propionate (3HP), 3-hydroxy butyrate (3HB), 3-hydroxy valerate (3HV), 3-hydroxyhexanoate (3HHx), 3-hydroxy heptanoate, 3-hydroxy octanoate, 3-hydroxy nonanoate, 3-hydroxy decanoate, 3-hydroxy undecanoate, 3-hydroxy dodecanoate, 3-hydroxy dodecenoate, 3-hydroxy tetradecanoate, 3-hydroxy hexadecanoate, 3-hydroxy octadecanoate, 4-hydroxy butyrate (4HB), 4-hydroxy valerate, 5-hydroxy valerate, 6-hydroxy hexanoate, hydroxy laurylate, etc. Advantageously, it is possible according to the invention to include monomer units other than 3 HB, especially other than 3 HB as the main constituent (>50 percent of weight) of the PHA produced thereby.

A new microorganism (new strain) according to the present invention may be any microorganism that is capable of producing a PHA, comprising a 16S rRNA gene whose polynucleotide sequence shows 99% or more homology to a polynucleotide sequence represented by SEQ ID No: 1, having an optimum temperature of an activity temperature range for the growth and PHA production of said microorganism of at least 45° C. and being capable of growing at a pH of 6 to 10.

Preferably, the microorganism is an aerobic, Gram-negative, polar flagellate *bacillus* (baciliform bacterium) being tolerant of catalase, oxidase, arginine dihydrolase in 4% NaCl at 37° C., 4% NaCl at 50° C. and/or is capable of assimilating sodium citrate, sodium pyruvate, sodium succinate, sodium acetate, sodium propionate, sodium caproate, sodium malate, betaine, L-lysine, L-asparagine, L-serine, L-glutamine, L-alanine, L-isoleucine, L-proline, dodecane, tridecane, hexadecane, nonadecane, eicosane, palmitic acid, octanal, 1-octanol, lauryl alcohol, Tween 80 and sodium benzoate. Specifically, the new microorganism belongs to genus *Pseudomonas*, genus *Thiobacillus*, genus *Vibrio*, genus *Xanthomonas*, genus *Acidovorax*, genus *Comamonas*, genus *Gluconobacter*, genus *Rhizobium* or genus *Zoogloea*.

In this invention, the term "microorganism" can be replaced with "fungus," "strain," "microorganism strain" or "bacterium." Thus, "new microorganism" can be expressed as "new strain."

A new microorganism of this invention has an optimum temperature of an activity temperature range at least 45° C., and this temperature range provides sufficient microorganism's growth and PHA production in a microbial cell body.

The following Examples describe a new microorganism that is capable of producing a PHA and is not classified as known species belonging to genus Pseudomonas. The new microorganism is named Pseudomonas sp. SG4502 strain (hereinafter briefly called "this strain" or "SG4502"). The new microorganism was deposited at the National Institute of Technology and Evaluation, Patent Microorganisms Depositary (an international depositary authority) on Jun. 2, 2008, and provided with acceptance number NITE BP-578. The new microorganism can be obtained from the international depositary authority upon request.

A new microorganism according to the present invention is isolated from the periphery of an apparatus for producing biodiesel fuel (BDF). Partial polynucleotide sequences of a 16S rRNA gene of the new microorganism according to the present invention are disclosed herein (see SEQ ID No: 1). Based on the gene sequence information, persons skilled in the art can readily synthesize a probe and a primer targeted at the 16S rRNA gene of the new microorganism of this invention, detect and even isolate a target fungus in BDF or BDF by-product (BDFB). The 16S rRNA gene can be specifically amplified by PCR method and its production volume can be determined as well.

Moreover, by separating a mixture of nucleic acids obtained by amplifying a highly conserved rRNA region by denaturant concentration gradient gel electrophoresis (DGGE), the sequences of separated nucleic acids are determined and the concentration is measured, thereby finding the microflora structure that shows the abundance ratio of the same or relative type of a group of microorganisms in the given sample. The gene detection method by targeting the 16S rRNA of this invention may be any other detection method for finding out a gene concerned, such as a method using a probe of the 16S rRNA gene or PCR method using the 16S rRNA gene as a template.

A microorganism according to the present invention may be any other microorganism comprising SG4502, like a variant mutated by natural or artificial means or its offspring.

On the other hand, a microorganism of this invention includes a 16S rRNA gene (16S rDNA) whose polynucleotide sequence shows 99% or more homology to a partial polynucleotide sequence represented by SEQ ID No: 1. In general, if the homology to a partial polynucleotide sequence (approx. 500 bp) of 16S rRNA gene (16S rDNA) in a compared microorganism is 99% or more, it is highly possible that the microorganism thereof belongs to the same genus.

At this point, a species of microorganisms are genealogically showing 70% or more DNA-DNA homology according to the following documents (a report of the Ad Hoc Committee of International Committee on Systematic Bacteriology by L. G. Wayne, D. J. Brenner, R. R. Colwell, P. A. D. Grimont, O. Kandler, M. I. Krichevsky, L. H. Moore, W. E. C. Moor, R. G. E. Murray, E. Stackebrandt, M. P. Starr and H. G. Truper, and a report of the adhoc committee on reconciliation of approaches to bacterial systematics, International Systematic Bacteriology, 37, pp. 463-464, 1987). E. Stackerbrandt et al. examined the relationship between the above-defined DNA-DNA homology and the homology to the full length of 16S rDNA. This comparison yields a correspondence between 70% or more DNA-DNA homology and 97% or more homology to the full length of 16S rDNA, and microorganisms having the 97% or more homology to the full length of 16S rDNA can be classified as the identical species. (Stackebrandt, E. and Goebel, B. M.: Taxonomic note: a place for DNA-DNA reassociation and 16S rRNA sequences analysis in the present species definition in bacteriology. Int. J. Syst. Bacteriol., 44, pp. 846-849, 1994).

More specifically, in view of the relationship between the above-mentioned homology to the full length of 16S rDNA and the species to be determined, if a polynucleotide sequence of the full length of 16S rDNA is identified, SG4502 and other strains having the 97% or more homology to the full length of 16S rDNA are defined as the identical species and included as microorganisms of this invention.

Next, in this invention, in cases where it is said that "one or more amino acids are deleted, substituted, inserted and/or added", the number of amino acids to be deleted, substituted, inserted and/or added is not particularly limited if a protein having amino acid sequences thereof includes desired functions, but for example 1 to 20, preferably 1 to 15, more preferably 1 to 10, and much more preferably 1 to 5 amino acids are deleted, substituted, inserted and/or added. If the identical or similar amino acid sequences are encoded, much more amino acids may be deleted, substituted, inserted and/or added.

In this invention, there are provided amino acid sequences showing a high homology with all amino acid sequences represented by SEQ ID No: 3 or SEQ ID No: 5 or partial amino acid sequences represented by SEQ ID No: 3 or SEQ ID No: 5 excluding at least signal sequences, and comprises amino acid sequences encoded proteins having PHA synthase activity. This "high homology" is at least 50% or more identity, preferably 70% or more identity, more preferably 80% or more identity, much more preferably 90% or more identity and most preferably 95% or more identity.

In this invention, "one or more amino acids are deleted, substituted, inserted and/or added" and "amino acid sequence identity (percentage; %)" are that amino acid sequences may be aligned and a gap may be introduced thereinto to obtain the maximum percentage (%) amino acid sequence identity (i.e. homology), and defined as the ratio of amino acid residues in a candidate sequence that are identical to amino acid residues encoded by the PHA synthase I gene or the PHA synthase II gene. Conservative substitution doesn't provide partial amino acid sequence homology. This percentage (%) can be searched and analyzed by algorithms and programs known to persons skilled in the art, such as DNASIS, BLAST, BLAST-2, ALIGN, JALVIEW, and DNASTAR software. Persons skilled in the art can determine appropriate parameters to measure amino acid sequences comprising any algorithm required.

Next, "stringent condition" in this invention is, if not otherwise indicated, the use of 6M urea, 0.4% SDS and 0.5×SSC or its equivalent hybridization condition, and if needed, more stringent condition may be imposed, like the use of 6M urea, 0.4% SDS and 0.1×SSC or its equivalent hybridization condition. Under each condition, the temperature can be set at about 40° C. or more. If more stringent condition is required, the temperature may range from about 50° C. to 65° C. Polynucleotide sequences can be hybridized according to a method described in the 2nd Edition of Molecular Cloning, etc.

Also, in this invention, in cases where it is said that "one or more nucleotides are deleted, substituted, inserted and/or added", the number of nucleotides (bases) to be deleted, substituted, inserted and/or added is not particularly limited if a protein encoded by polynucleotide sequences (base sequences) thereof has desired functions, but for example 1 to 20, preferably 1 to 15, more preferably 1 to 10, and much more preferably 1 to 5 may be deleted, substituted, inserted and/or added. If the identical or similar amino acid sequences are encoded, much more nucleotides may be deleted, substituted, inserted and/or added.

In this invention, there are provided polynucleotide sequences showing a high homology with polynucleotide sequences represented by SEQ ID No: 2 or SEQ ID No: 4, and comprises polynucleotide sequences encoding a protein having PHA synthase activity. This "high homology" is at least 50% or more identity, preferably 70% or more identity, more preferably 80% or more identity, much more preferably 90% or more identity and most preferably 95% or more identity.

In this invention, "one or more nucleotide sequences are deleted, substituted, inserted and/or added" and "polynucleotide sequence identity (percentage; %)" means that polynucleotide sequences may be aligned and a gap may be introduced thereinto to obtain the maximum percentage (%) polynucleotide sequence identity (i.e. homology), and defined as the ratio of nucleotide sequences in a candidate sequence that are identical to nucleotide sequences comprised in the PHA synthase I gene or the PHA synthase II gene. This percentage (%) can be searched and analyzed by algorithms and programs known to persons skilled in the art, such as DNASIS, BLAST, BLAST-2, ALIGN, JALVIEW, and DNASTAR software. Persons skilled in the art can determine appropriate parameters to measure polynucleotide sequences comprising any algorithm required.

Genes of this invention can be cloned by known techniques. Chromosomal DNA can be prepared, for example, according to described in Current Protocols in Molecular Biology unit 2-4, and DNA Cloning 1: Core Techniques, A Practical Approach, Second Edition, Oxford University Press (1995), etc, and using commercial kits such as DNeasy Blood & Tissue Kit (QIAGEN), The illustra bacteria genomic Prep Mini Spin Kit (GE Healthcare) and PrepMan Ultra Reagent {Applied Biosystems Japan (ABI)}.

A target gene can be amplified and obtained by polymerase chain reaction (PCR), using the obtained chromosomal DNA as a template. The gene can be cloned into an appropriate vector by conventional methods.

Host cells employed in this invention include animal cells, fungus, yeast, *Escherichia coli*, Gram-positive bacteria such as genus *Actinoplanes*, genus *Alicyclobacillus*, genus *Corynebacterium*, genus *Brevibacterium*, genus *Lactobacillus*, genus *Mycobacterium*, genus *Mycoplasma*, genus *Bacillus*, genus *Clostridium*, genus *Deinococcus*, genus *Streptomyces*, genus *Staphylococcus*, genus *Enterococcus* and genus *Streptococcus*, Gram-negative bacteria such as genus *Escherichia*, genus *Salmonella*, genus *Agrobacterium*, genus *Azotobacter*, genus *Methylobacterium*, genus *Pseudomonas*, genus *Rhodopseudomonas*, genus *Zymomonas*, genus *Chloropseudomonas*, genus *Flavobacterium*, genus *Myxococcus*, genus *Nannocystis*, genus *Borrelia*, genus *Ralstonia*, genus *Alcaligenes* and genus *Aeromonas*, photosynthetic Gram-negative bacteria such as genus *Chromatium* and genus *Rhodospirillum*, archaebacteria such as genus *Archaeoglobus*, genus *Methanobacterium*, genus *Methanococcus*, genus *Pyrococcus*, genus *Cardarella*, genus *Halobacterium* and genus *Sulfolobus*, blue-green algae such as genus *Anabaena*, genus *Anacystis*, genus *Phormidium*, genus *Synecoccus* and genus *Synecocystis*, and green algae such as genus *Chlorella* and genus *Scenedesmun*.

A cloning vector employed in this invention is not particularly limited, but favorably the one having the capability to be autonomously-replicating in *Escherichia coli*, such as phage vector and plasmid vector, more specifically ZAP Express (Stratagene), pBluescript II SK(+) (Nucleic Acids Research), Lambda ZAP II (Stratagene), λgt10, λgt11 (DNA Cloning, A Practical Approach), λTriplEx (Clontech), λExCell (Pharmacia), pT7T318U (Pharmacia), pTrc99A (Pharmacia), pKK223-3 (Pharmacia), pcD2 (H. Okayama and P. Berg), pMW218 (Wako), pUC118 and 119 (Takara), pUC18 and 19 (Takara), pSTV28 and 29 (Takara), pEG400 (J. Bac.), pQE-30 (QIAGEN), pQE80 (QIAGEN), pTA2 (TOYOBO), pGEM-T (Promega) and pGEM-T eazy (Promega). Moreover, shuttle vectors can be used as a cloning vector, as well as vectors that can be autonomously-replicating with two or more types of host microorganisms, such as *Escherichia coli* and genus *Pseudomonas*. Such cloning vectors can be cut with the above restriction enzyme to obtain its fragment.

A DNA fragment is linked to a vector fragment, using a known DNA ligase. This operation requires annealing to prepare a recombinant vector.

A recombinant vector can be introduced into a host microorganism by known methods. If a host microorganism is *Escherichia coli*, such known methods include calcium chloride method {Current Protocols in Molecular Biology unit 1-4, Lederberg, E. M. et al., J. Bacteriol. 119, 1072 (1974)}, electroporation method (Current Protocols in Molecular Biology, volume 1, pages 1.8.4, 1994), protoplast method (Japanese Unexamined Patent Application Publication No. 1988-2483942) and a method described in Gene, 17, 107 (1982), Molecular & General Genetics, 168, 111 (1979). If a host microorganism is phage DNA, known methods like in vitro packaging method (Current Protocols in Molecular Biology, volume 1, pages 5.7.1, 1994) can be used. As competent cells, commercial kits from Takara, TOYOBO, NIPPON GENE, Invitrogen, Stratagene, etc. can be used. In this invention, in vitro packaging kits (e.g. Gigapack III Gold; Stratagene) may be employed.

From a transformant obtained, a plasmid comprising a target DNA can be obtained by conventional methods as shown in Molecular Cloning, the 2nd Edition, Current Protocols in Molecular Biology, DNA Cloning 1: Core Techniques and A Practical Approach, Second Edition, Oxford University Press (1995).

Meanwhile, several amino acid sequences of PHA synthase are currently known {Gabriel J. McCool and Maura C. Cannon, J. Bacteriol., 181, 585 (1999); Liebergesell, M. and Steinbuchel, Eur. J. Biochem., 209, 135 (1992); Kaneko, T., et al., DNA Res., 3, 109 (1996); Liebergesell, M. and Steinbuchel, Appl. Microbiol. Biotechnol., 38, 493 (1993), etc}. In such known amino acid sequences, highly preserved regions are selected and nucleotide sequences encoding the regions are estimated for the design of oligonucleotide.

Next, nucleotide sequences of a DNA fragment can be determined by known methods like Sanger method (Molecular Cloning, volume 2, page 13.3, 1989) by nucleotide sequence autoanalyzer. In this operation, several types of synthetic DNA are used as a primer, along with BigDye Terminator v3.1 Cycle Sequencing Kit (ABI), DYEnamic ET Terminator Cycle Sequencing Kit (GE Healthcare) and DNA Sequencer (ABI) by conventional methods.

Genes of this invention can be obtained by chemical synthesis, PCR method (using a chromosomal DNA as a template), or hybridizing polynucleotide sequences using a DNA fragment having at least a part of the polynucleotide sequence as a probe.

Next, a gene expression cassette of this invention comprises a promoter, a gene having PHA synthase activity and PHA-degrading enzyme activity (e.g. one or more DNAs selected from the group consisting of a PHA synthase I gene, a PHA synthase II gene and a PHA-degrading enzyme gene) and a terminator corresponding to the promoter, all of which are linked from a 5' upstream region to a 3' downstream region. By incorporating the gene expression cassette into one or more recombinant vectors to be introduced into a host, a transformant according to this invention can be obtained and the expression thereof can be adjusted. As example of a PHA-degrading enzyme gene, reference is made to polynucleotide and polypeptide shown in SEQ ID Nos. 6 and 7, respectively.

A transformant of this invention can be obtained by transforming and transducing the recombinant vectors incorporating a gene expression cassette of this invention into the host. The host is not particularly limited if the target gene can be expressed (e.g. microorganisms belonging to genus *Alcaligenes*, microorganisms belonging to genus *Pseudomonas*, microorganisms belonging to genus *Bacillus*, bacteria like *Escherichia coli*, yeasts like genus *Saccharomyces* and genus *Candida*, and animal cells such as COS cells and CHO cells).

Preferably, if *Escherichia coli*, etc. are used as a host, a recombinant DNA of this invention can be autonomously-replicating in the host and comprises a promoter, DNAs of this invention and transcription termination sequences. The expression vector can be pLA2917 (ATCC 37355) having an origin of replication of RK2 replicated and conserved in various types of hosts, and pJRD215 (ATCC 37533), pBBR122 (MoBiTec GmbH) and pBHR1 (MoBiTec GmbH), each having an origin of replication of RSF1010, etc.

A promoter is not particularly limited if the promoter can be expressed in the host (e.g. *Escherichia coli*- or phage-derived promoters such as trp promoter, lac promoter, trc promoter, $P_L$ promoter, $P_R$ promoter, $P_{SE}$ promoter and T5 promoter, and $SPO_1$ promoter, $SPO_2$ promoter and penP promoter. Also, artificially designed and modified promoters like a promoter in which 2 Ptrp are linked in series, tac promoter, letI promoter and lacT7 promoter can be used. A recombinant DNA can be introduced into a bacterium by calcium ion method (Current Protocols in Molecular Biology, volume 1, pages 1.8.1, 1994) and Electroporation method (Current Protocols in Molecular Biology, volume 1, pages 1.8.4, 1994), etc.

If a yeast is used as a host, the expression vector can be like YEp13 and YCp50. The promoter can be used, like gall promoter and gal10 promoter. A recombinant DNA can be introduced into the yeast by Electroporation method {Methods Enzymol., 194, 182-187 (1990)}, Spheroplast method {Proc. Natl. Acad. Sci. USA, 84, 1929-1933 (1978)}, Lithium Acetate method {J. Bacteriol., 153, 163-168 (1983)}, etc.

If an animal cell is used as a host, the expression vector can be used like pcDNAI and pcDNAI/Amp (Invitrogen). A recombinant DNA can be introduced into the animal cell by Electroporation method, Calcium Phosphate method, etc.

Next, a PHA synthase of this invention is collected from a culture (cultured cells or culture supernatants), in which the PHA synthase is produced and accumulated, by culturing a bacterium or variant of this invention. The bacterium and variant of this invention are cultured by a conventional method.

A PHA of this invention is collected from a culture or cultured cells, in which the PHA is produced and accumulated, by culturing a bacterium or variant of this invention. The bacterium and variant of this invention are cultured by a conventional method.

A medium for culturing a bacterium or variant is complete medium or synthetic medium, such as LB medium and M9 medium. PHA synthase and PHA can be accumulated and collected in a microbial cell body by aerobically culturing such a bacterium or variant with a pH of 7 to 9 and at a temperature of 30 to 50° C. for 4 to 24 hours.

A PHA synthase can be refined from the culture after culturing completely, using a sampling means, e.g. by crushing a microbial cell body by conventional ultrasonic fragmentation, or lysing the microbial cell body to extract synthase using lytic enzyme like lysozyme. Crude enzymes thus obtained are refined, using chromatography, such as ion-exchange chromatography and gel filtration chromatography.

A PHA can be refined from a microbial cell body or variant according to the following operations. After collecting the microbial cell body and variant from a culture solution by centrifugal separation and washing them with distilled water, they are dried. Afterward, the dry microbial cell body and variant are suspended in chloroform and the product is heated to extract PHA. Residues are removed by filtration. By adding methanol to the chloroform solution, PHA is precipitated. After removing supernatants by filtration or centrifugal separation, PHA is dried and refined.

Next, a new microorganism according to the present invention is capable of producing poly-3-polyhydroxyalkanoate {P(3HA)} using α-unsaturated fatty acid as a substrate, and specifically producing poly-3-hydroxyhexanoate{P(3HHx)} using 2-hexenoic acid as a substrate and producing poly-3-hydroxybutyrate{P(3HB)} using crotonic acid as a substrate. A α-unsaturated fatty acid of this invention is, e.g. 2-hexenoic acid, crotonic acid, acrylic acid, 2-pentanoic acid, 2-octenoic acid, 2-decenoic acid, 2-heptenoic acid and 2-nonenoic acid. Advantageously, it is possible according to the invention to include monomer units other than 3 HB, especially other than 3 HB as the main constituent (>50 percent of weight) of the PHA produced thereby.

EXAMPLE

Specific examples of this embodiment in this invention will be further described with regard to a new microorganism capable of producing a PHA, a PHA synthase gene, an expression cassette comprising the gene, a vector comprising the expression cassette, a transformant transformed by the vector, a polypeptide having PHA synthase activity, a method for producing a PHA synthase and a method for producing a PHA as follows. The technical scope of this invention is not limited to the characteristics shown by these examples.

Example 1

The inventors isolated a PHA-producing bacterium from the periphery of an apparatus for producing biodiesel fuel (BDF) according to the following method, and identified this strain.

<Isolation of PHA-Producing Bacterium>

Specifically, dirt that was found at the periphery of an apparatus for producing BDF (like floor, drain outlet and side face of wastewater tank) was sampled with a spatula and the sample was put into 10 mL of sterile water and the product was subjected to centrifugal separation (1000×g) at room temperature for 3 minutes to obtain supernatants. 100 µL of the supernatants was inoculated into 50 mL of MS medium containing 1 weight % of BDFB (neutralized BDFB) obtained by neutralizing with sulfuric acid and the product was subjected to enrichment culture at 45° C. for 3 days. 100 µL of the culture solution was added to 50 mL of MS medium containing I weight % of another neutralized BDFB to culture bacteria at 45° C. After streaking the culture solution on an NR agar plate medium and culturing the bacteria at 45° C. for 3 days, a strain was isolated from a colony formed on the NR agar plate medium. The isolated strain was inoculated into 2 mL of NR medium and the product was subjected to shaking culture at 45° C. overnight and was lyophilized.

Next, 5 mL of the culture solution was added to 500 mL baffle flask (IWAKI) containing 100 mL of MS medium to culture the bacteria at 45° C. at a speed of 160 rpm for 48 hours. When the culturing started and 24 hours elapsed, neutralized BDFB was added to be 1% (wt/vol). After the culture solution was subjected to centrifugal separation, the bacteria therein were washed with distilled water, followed by 100% methanol and distilled water again and were lyophilized. The lyophilized microbial cell body was treated with methanolysis to detect polymer accumulation by gas chromatograph method. The strain, in which polymer accumulation was found, was selected as a PHA-producing-strain by neutralized BDFB as a carbon source.

The compositions of an NR medium and an MS medium employed in this Example are as follows {J. Bacteriol. V179, pp. 4821-4830 (1997), Appl. Microbiol. Biotechnol. V45, pp. 363-370 (1996)}.

| (Compositions of NR medium) in 1 L of medium | |
|---|---|
| Bacto yeast extracts | 3 g |
| Bacto peptone | 10 g |
| Ehrlich bonito extracts | 10 g |

| (Compositions of MS medium) in 1 L of medium | |
|---|---|
| Disodium hydrogen phosphate | 3.6 g |
| Potassium dihydrogen phosphate | 1.5 g |
| Ammonium chloride | 0.5 g |
| Magnesium sulphate heptahydrate | 0.0104 g |
| Trace element aqueous solution | 0.05 mL |

<Identification of *Pseudomonas* sp. SG4502>
(1) Mycological Property Test

Using the isolated strains, mycological property test was performed by Japan Food Research Laboratories. The results are described as follows.

| 1) Morphological properties On standard agar medium, at 45° C. Morphological characteristics | |
|---|---|
| 1. Cell morphology | bacilliform |
| 2. Mobility | found |
| 3. Gram staining | negative |
| 2) Physiological properties | |
| 1. Catalase | + |
| 2. Oxidase | + |
| 3. Nitrate reduction | − |
| 4. Anaerobic growth with nitrate | − |
| 5. Denitrification | − |
| 6. Urease | − |
| 7. Arginine dihydrolase | + |
| 8. Polar flagella | + |
| 9. Hydrolysis | |
| 9-1. Esculin | − |
| 9-2. Gelatin | − |
| 9-3. Starch | − |
| 9-4. Skim milk | − |
| 9-5. Tween 20 | + |
| 9-6. Tween 80 | + |
| 10. Growth with 3% NaCl | + |
| 11. Growth with 4% NaCl (37° C.) | + |
| 12. Growth with 4% NaCl (50° C.) | + |
| 13. Growth with pH5 | − |
| 14. Growth with pH6 | + |
| 15. Growth with pH10 | + |
| 16. Growth with pH11 | − |
| 17. Growth at 46° C. | + |
| 18. Growth at 50° C. | + |
| 19. Assimilating property test | |
| 19-1. Fructose | − |
| 19-2. D-mannose | − |
| 19-3. D-trehalose | − |
| 19-4. D-cellobiose | − |
| 19-5. L-arabinose | − |
| 19-6. D-glucose | − |
| 19-7. L-sorbose | − |
| 19-8. D-sucrose | − |
| 19-9. D-xylose | − |
| 19-10. D-maltose | − |
| 19-11. Potassium gluonate | − |
| 19-12. Phenyl acetate | − |
| 19-13. Sodium citrate | + |
| 19-14. Sodium adipate | − |
| 19-15. D-mannitol | − |
| 19-16. Glycerol | − |
| 19-17. Sodium pyruvate | + |
| 19-18. Sodium succinate | + |
| 19-19. Sodium acetate | + |
| 19-20. Sodium propionate | + |
| 19-21. Sodium caproate | + |
| 19-22. Sodium malate | + |
| 19-23. Betaine | + |
| 19-24. L-lysine | + |
| 19-25. Glycine | − |
| 19-26. L-cysteine | − |
| 19-27. L-phenylalanine | − |
| 19-28. L-histidine | − |
| 19-29. L-asparagine | + |
| 19-30. L-arginine | − |
| 19-31. L-serine | + |
| 19-32. L-glutamine | + |
| 19-33. L-alanine | + |
| 19-34. L-isoleucine | + |
| 19-35. L-proline | + |
| 19-36. N-acetylglucosamine | − |
| 19-37. Decane | − |
| 19-38. Dodecane | + |
| 19-39. Tridecane | + |
| 19-40. Hexadecane | + |
| 19-41. Nonadecane | + |
| 19-42. Eicosane | + |
| 19-43. Palmitic acid | + |
| 19-44. Octanoic acid | − |
| 19-45. Octanal | + |
| 19-46. 1-octanol | + |
| 19-47. Lauryl alcohol | + |
| 19-48. Tween 80 | + |
| 19-49. SDS | − |
| 19-50. Sodium benzoate | + |
| 19-51. Sodium salicylate | − |
| 19-52. Naphthalene | − |
| 19-53. Anthracene | − |
| 19-54. Phenanthrene | − |

This strain was found to be *Pseudomonas* sp. with reference to International Journal of Systematic and Evolutionary Microbiology (2002) 53, pp. 2203-2209, based on the mycological characteristics of this Example (1).

(2) Polynucleotide Sequence Analysis

Next, in this strain isolated, partial nucleotide sequence of a 16S rRNA gene was determined. Using MicroSeq 500 16S rDNA PCR Kit (ABI), the 16S rRNA gene was amplified by PCR and nucleotide sequence of the amplified gene were analyzed using MicroSeq 500 16S rDNA Sequencing Kit (ABI). The polynucleotide sequence is shown in SEQ ID No: 1.

(3) Taxonomic Consideration

Subsequently, partial polynucleotide sequence (SEQ ID No: 1) of this Example (2) were compared to known genes in the gene database obtained by BLAST search (Altschul, S. F. et al., Basic local alignment search tool. J. Mol. Biol. 215, 403-410), thereby finding out the following sequences of *Pseudomonas thermotoleran* strain CM3$^T$.

The partial polynucleotide sequence of the 16S rRNA gene of *Pseudomonas thermotolerans* strain CM3$^T$ showed 99% homology to the polynucleotide sequence of SEQ ID No: 1. However, it has not been confirmed that this microorganism is a PHA-producing strain. Moreover, the results of bacterial growth with 4% sodium chloride (at 37° C.) and those of assimilating property test for sodium citrate, sodium pyruvate, sodium succinate, L-lysine, L-arginine, octanoic acid and SDS demonstrated no correspondence with the properties of *Pseudomonas thermotoleran* strain CM3$^T$. From these observations, this strain is a new microorganism, named as *Pseudomonas* sp. SG4502, and was deposited at the National Institute of Technology and Evaluation, Patent Microorganisms Depositary (an international depositary authority) on Jun. 2, 2008, with accession number NITE BP-578.

Example 2

PHA Production by *Pseudomonas* sp. SG4502

PHA was produced, using SG4502 isolated and identified in the above Example 1. By changing the type of a carbon source to be added to a culture medium in this operation, PHA production volume, PHA molecular structure, molecular weight and compositions (monomer composition ratio) were compared and discussed by carbon source.

Specifically, after a frozen SG4502 was inoculated into 2 mL of NR medium to culture bacteria at 45° C. for 8 hours, the culture solution was inoculated into another 100 mL of NR medium and the product was subjected to shaking culture overnight. 60 mL of the culture solution was added to 3 L Erlenmeyer flask (IWAKI) containing 1.2 L of MS medium and the product was subjected to shaking culture at 45° C., 37° C. and 30° C. 1% (wt/vol) carbon source was added to the 3 L Erlenmeyer flask when the culturing started and 12, 24 and 36 hours elapsed, and the carbon source added was sodium dodecanoate, sodium octanoate, sodium acetate or neutralized BDFB for culturing the bacteria at 45° C., respectively. The carbon source was neutralized BDFB in culturing at 37° C. and 30° C. 48 hours after culturing at every temperature, each culture solution was subjected to centrifugal separation (8000×g) at 4° C. for 15 minutes to collect a microbial cell body. Then, the microbial cell body was washed with 20% ethanol aqueous solution, followed by 100% ethanol aqueous solution and distilled water, and was lyophilized and dried. FIG. 1 shows dry microbial cell body volume.

(1) PHA Extraction

After a PHA was extracted from each dry microbial cell body obtained, using Soxhlet extractor (Shibata) with chloroform as a solvent, PHA product was obtained by removing the solvent by the evaporator and vacuum-drying the PHA. FIG. 1 shows PHA production volume.

As shown in FIG. 1, PHA was produced using neutralized BDFB as a carbon source, whose volume is equivalent to or more than that by sodium acetate, sodium octanoate or sodium dodecanoate.

(2) Molecular Structure Analysis

The molecular structure of each PHA obtained was analyzed by $^1$H-NMR (nuclear magnetic resonance (NMR)). In NMR measurement, MSL400 spectroscope of Brucker Corporation was employed, with a frequency of 400 MHz NMR at 25° C. FIGS. 3 to 6 show $^1$H-NMR spectrum of each PHA using sodium dodecanoate, sodium octanoate, sodium acetate or neutralized BDFB as a carbon source.

Figure 4:
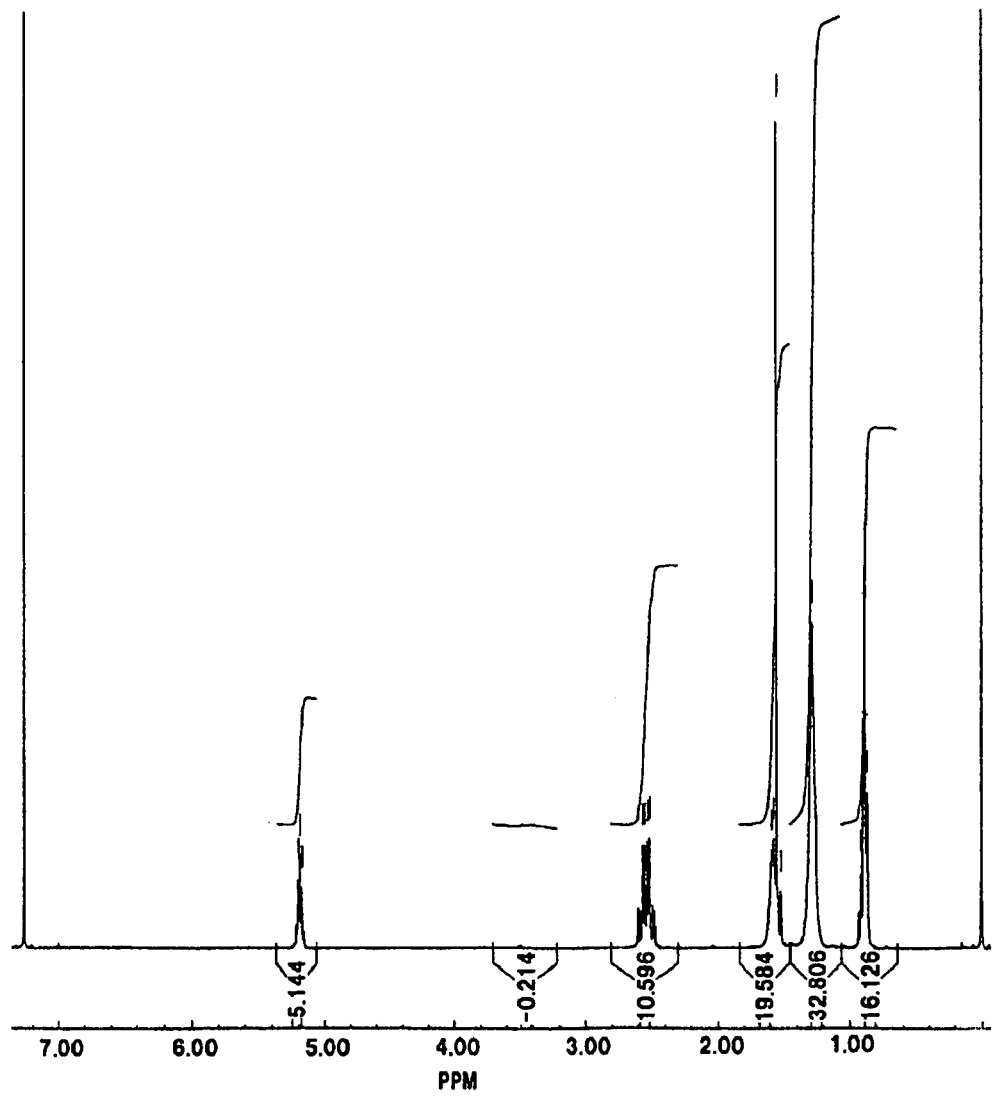
FIG. 4 is a diagram showing $^1$H-NMR spectrum of a compound produced by SG4502 in Example 2 (2), using sodium octanoate as a carbon source.
Figure 5:
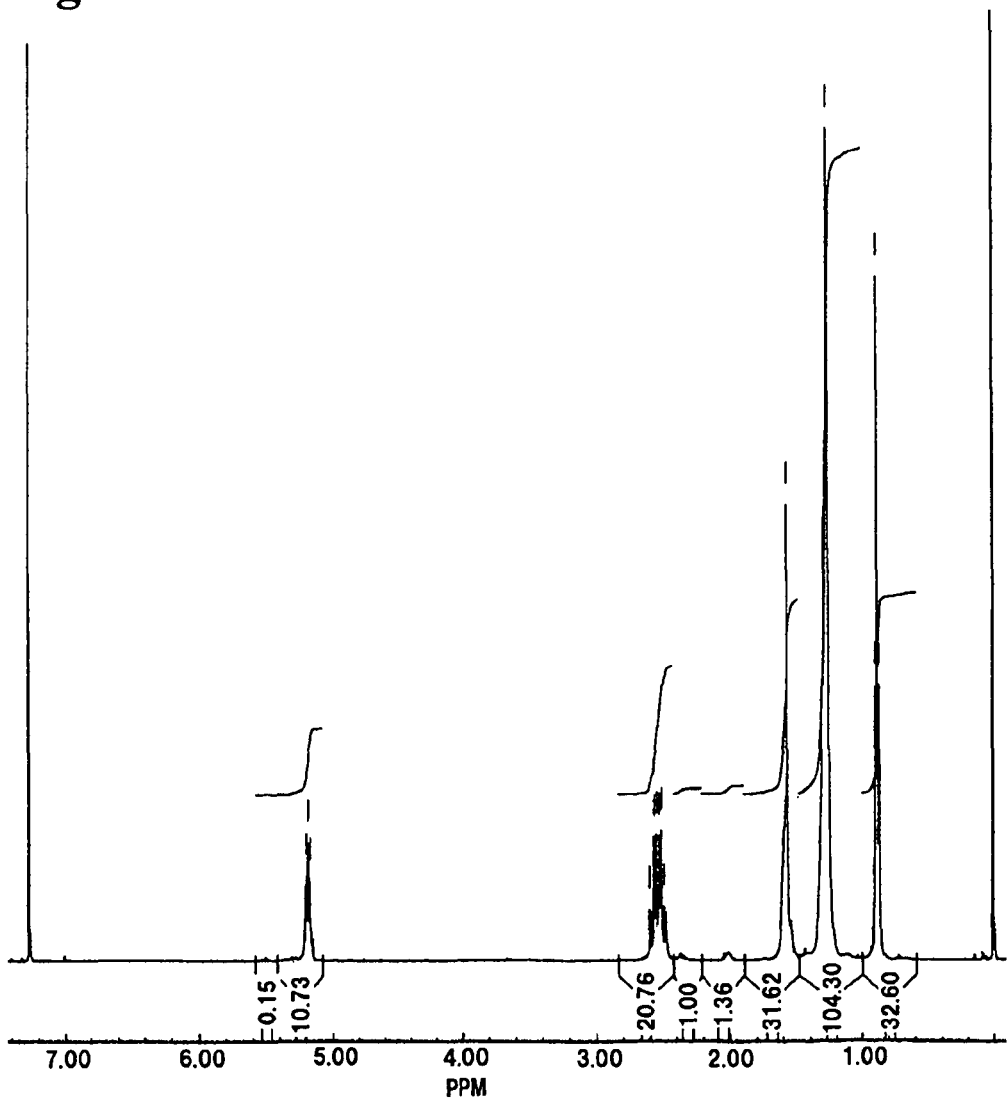
FIG. 5 is a diagram showing $^1$H-NMR spectrum of a compound produced by SG4502 in Example 2 (2), using sodium acetate as a carbon source.
Figure 6:
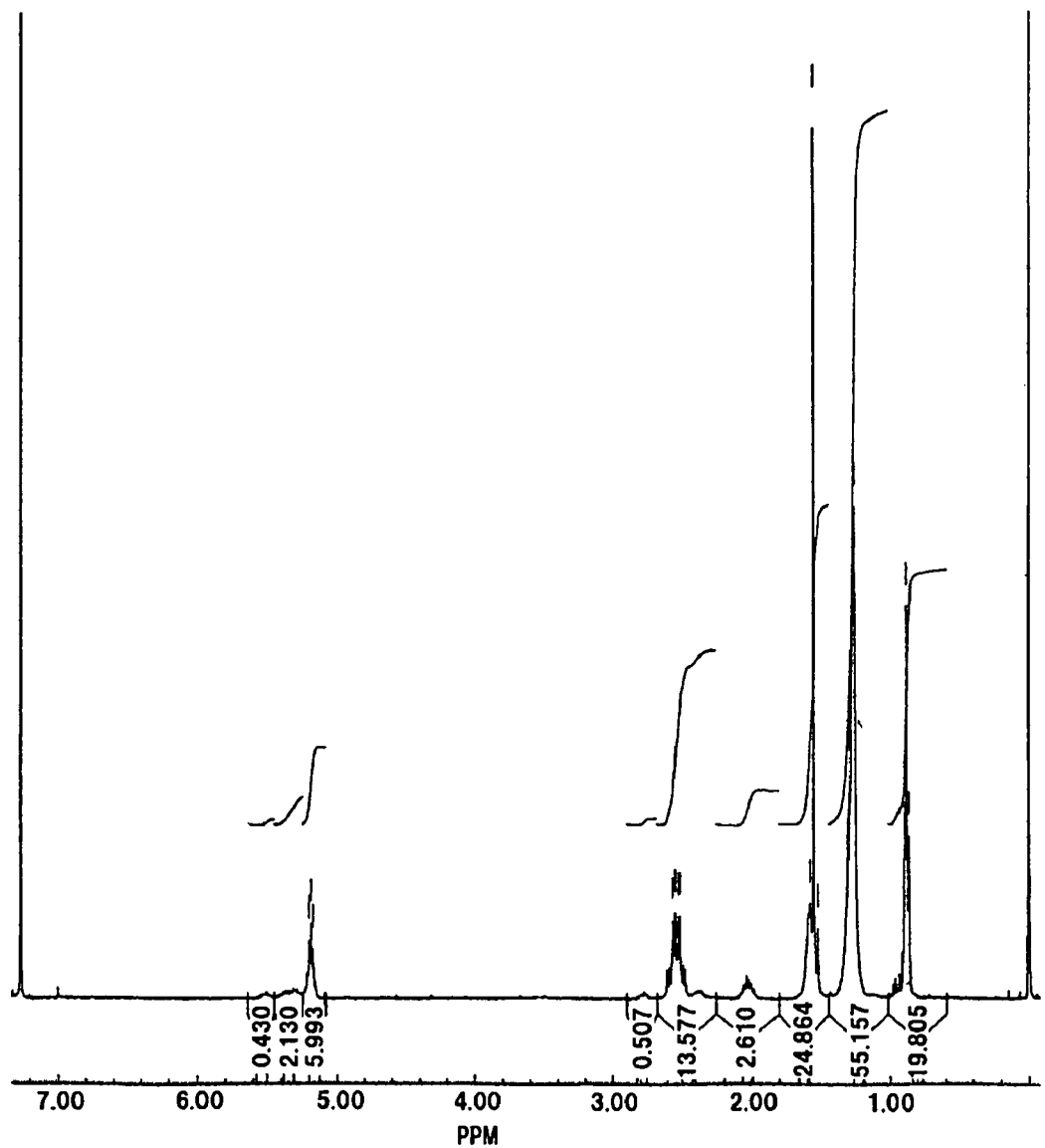
FIG. 6 is a diagram showing $^1$H-NMR spectrum of a compound produced by SG4502 in Example 2 (2), using neutralized biodiesel fuel by-product (neutralized BDFB) as a carbon source.

As shown in FIGS. 3 to 6, every product was found to be PHA. As shown in FIGS. 3 to 5, PHA, produced using sodium acetate, sodium octanoate or sodium dodecanoate as a carbon source, was found to be a polymer having no unsaturated bond. As shown in FIG. 6, it was found that PHA produced with neutralized BDFB as a carbon source is a copolymer comprised a monomer unit having no unsaturated bond and a monomer unit having unsaturated bond.

(3) Molecular Weight Measurement

Subsequently, molecular weight of each PHA obtained was measured by gel permeation chromatography (GPC). In this measurement, two TSK gel Super HZM-H columns (6.0 mm I.D.×150 mm; Tosoh Co., Tokyo) were linked in series with each other. The mobile phase was chloroform and the molecular weight was measured with a flow rate of 0.3 mL/min at 40° C. The calibration curve was determined using pure polystyrene. In each PHA, number average molecular weight (Mn), weight-average molecular weight (Mw) and molecular weight distribution (Mw/Mn) were determined. FIG. 1 shows the measurement result.

As shown in FIG. 1, PHA produced using neutralized BDFB as a carbon source is lower in molecular weight than a PHA product from sodium dodecanoate, sodium octanoate or sodium acetate. The inventors assume that the result is caused primarily by glycerol contained in neutralized BDFB.

(4) Composition Analysis

The compositions of each PHA obtained were analyzed by gas chromatography method under the following conditions. First, each PHA was dissolved in a mixture of 2 mL of 15 weight % methanol sulfuric acid solution and 2 mL of chloroform, and the solution was treated with alcoholysis at 100° C. for 140 minutes. After cooling the solution, 1 mL of ultrapure water was added thereto, well mixed and allowed to stand to separate the solution into two layers. Subsequently, a lower layer thereof was collected and insoluble matter was removed by filtration. After mixture of 0.5 mL of the solution and 0.5 mL of chloroform solution containing 0.1 vol % methyl octanoate were analyzed by capillary gas chromatograph GC-2010 (Shimadzu Corporation) having FID to identify methyl ester compounds as a monomer unit. The column was a fused silica capillary column DB-5 (I.D.: 0.25 mm, liquid-phase film thickness: 0.25 μm, column length: 30 m; Shimadzu Corporation). The analysis was started at initial temperature of 90° C. (duration: 5 min.) and ended at final temperature of 250° C. (duration: 2 min.), with a temperature-rising rate of 5° C./min therebetween. FIG. 2 shows the results of analysis.

As shown in FIG. 2, the compositions of produced PHA vary according to carbon source. Monomer units having unsaturated bond in PHA produced with neutralized BDFB as a carbon source were not detected by gas chromatograph analysis, although the units were detected by $^1$H NMR analysis. The inventors assume that the content of the units in PHA is below detection limits of gas chromatograph analysis.

From the results in the above (2) to (4), SG4502 can be a strain that is capable of producing various types of PHA, using many carbon sources. More specifically, using SG4502, PHA can be selectively produced so as to have desired properties in accordance with its appropriate carbon source.

Example 3

Cloning of PHA Synthase Gene of *Pseudomonas* sp. SG4502

PHA synthase of SG4502 was cloned according to the following steps.

(1) Preparation of Chromosomal DNA of *Pseudomonas* sp. SG4502

First, SG4502 was cultured in 2 mL of sterilized NR culture solution at 45° C. overnight. 100 μL of the culture solution was put into 2 mL of another NR medium and the product was subjected to shaking culture at 45° C. until turbidity of the culture solution (absorbance: 600 nm) reached 0.7. After the culturing was completed, a microbial cell body was separated from the culture solution by centrifugal separation at a speed of 7000 rpm for 10 minutes and 100 μL of chromosomal DNA (120 ng/μL of DNA concentration) was prepared by DNeasy Blood & Tissue Kit (QIAGEN).

(2) Obtaining a DNA Fragment Containing PHA Synthase Gene

Next, in several known PHA synthase genes, two conserved regions were selected and DNA base sequence (polynucleotide sequence) encoding the conserved regions were estimated. Then, two types of oligonucleotides were synthesized with reference to FEMS Microbiology Letters (2001) 198, pp. 165-170. The nucleotide sequences are expressed as follows.

```
                                       (SEQ ID No: 8)
5' - ccatgacagc ggcctgttca cctg - 3'

(SEQ ID No: 9)
5' - tcgacgatca ggtgcaggaa cagcc - 3'
```

Using the oligonucleotides represented by the above SEQ ID No: 8 and SEQ ID No: 9 as a primer, polymerase chain reaction (PCR) was produced under the following conditions.
—Reaction Reagent—

A reaction reagent was prepared according to the manual for TaKaRa LA Taq with GC Buffer (Takara). 2×GC buffer solution I was used for producing the reaction, and 1 μL of the chromosomal DNA obtained in this Example (1) was used.
—Condition of the Reaction—

The PCR was performed in 10 cycles, each cycle comprising 1-minute reaction at 94° C., 30-second reaction at 94° C. and 5-minute reaction at 70° C., and subsequently in 20 cycles, each cycle comprising 30-second reaction at 94° C. and 5-minute reaction at 68° C., and finally additional 10-minute reaction at 68° C. Consequently, a DNA fragment (approx. 5.2 kbp) was amplified.

Next, the amplified DNA fragment was TA-cloned into a plasmid vector pCR2.1-TOPO, using TOPO TA Cloning kit with TOP 10 cells (Invitrogen) according to its manual. A transforming liquid was applied to LB agar medium containing ampicillin (final concentration: 100 μg/mL) and the product was subjected to static culture at 37° C. for 24 hours. A colony obtained was inoculated into 2 mL of LB medium and cultured at 37° C. overnight, and thereafter a plasmid DNA was prepared. The plasmid, named as pC1ZC2_SG4502, was deposited with the National Institute of Technology and Evaluation, Patent Microorganisms Depositary (an international depositary authority) on Nov. 18, 2008, with an accession number of NITE BP-579.

(3) Nucleotide Sequence Analysis for PHA Synthase Gene and Search of PHA Synthase Gene Subsequently, using the plasmid pC1ZC2_SG4502 as a template, nucleotide sequences of each DNA fragment were determined. This operation has been conducted with various types of synthetic DNA as a primer, using BigDye Terminator v3.1 Cycle Sequencing Kit (ABI) and DNA sequencers (ABI) by conventional methods. Using TA-cloned insert DNA and various types of synthetic DNA as a primer, polynucleotide sequences (approx. 5.2 kbp) of the PHA synthase gene were determined by dideoxy method.

In the polynucleotide sequences determined, 3 open reading frames were found by homology analysis, using ORF Finder for estimating gene regions and BLAST. Open reading frame 1 (ORF1) comprises 1680 bases, having approx. 89% of amino acid sequence identity (homology) with respect to amino acid sequences in a gene encoding Pseudomonas stutzeri-derived PHA synthase I {FEMS Microbiol. Lett. 234 (2), 231-237 (2004), Accession No. AY278219}. Open reading frame 2 (ORF2) comprises 906 bases, having approx. 95% of amino acid sequence identity with respect to amino acid sequences in a gene encoding Pseudomonas stutzeri-derived PHA-decomposing enzyme (same as above), and open reading frame 3 (ORF3) comprises 1692 bases, having approx. 90% of amino acid sequence identity with respect to amino acid sequences in a gene encoding Pseudomonas stutzeri-derived PHA synthase II (same as above).

Figure 7:
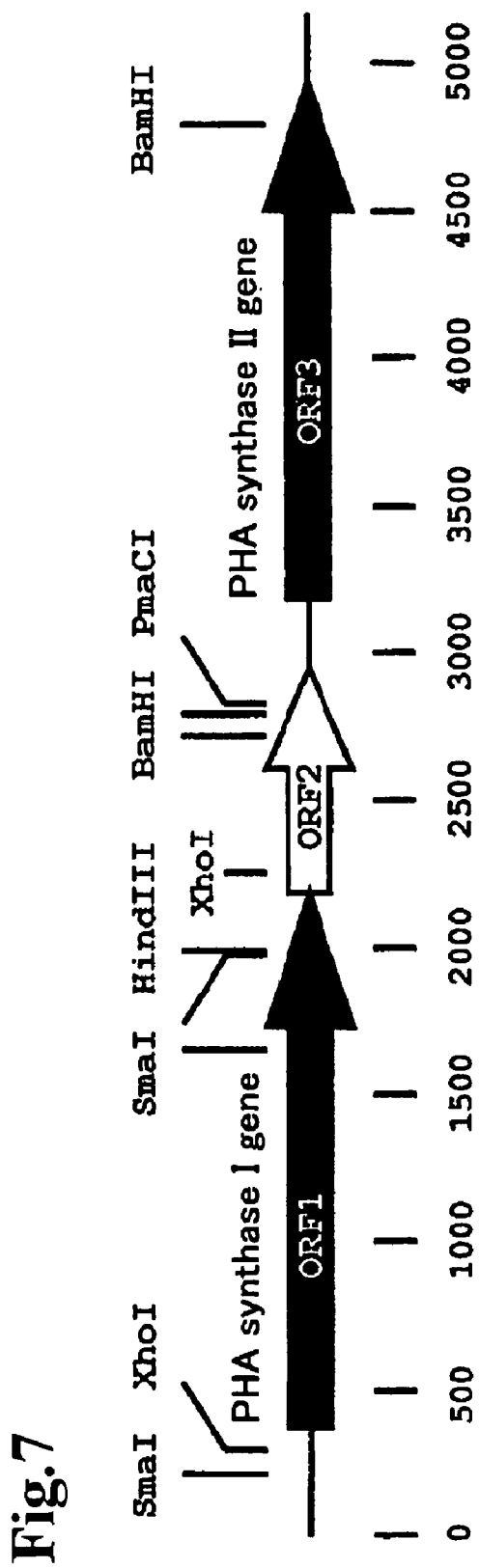
FIG. 7 is a diagram showing restriction map of DNA fragment (approx. 5.2 kb) derived from a *Pseudomonas* sp. SG4502 strain.

Based on the polynucleotide sequences obtained, a restriction map of SG4502-derived DNA fragment (aprox. 5.2 kb) cloned by pC1ZC2_SG4502 was prepared. FIG. 7 shows the restriction map.

ORF1 polynucleotide sequences are represented by SEQ ID No: 2, amino acid sequences encoded by the ORF1 in SEQ ID No: 3, ORF3 polynucleotide sequences in SEQ ID No: 4, amino acid sequences encoded by the ORF3 in SEQ ID No: 5, ORF2 polynucleotide sequences in SEQ ID No: 6, and linear sequences of amino acids of a polypeptide translated by polynucleotide sequences in SEQ ID No: 7. The ORF1 polynucleotide sequences were defined as PHA synthase I gene, and ORF3 polynucleotide sequences were defined as PHA synthase II gene.

Example 4

In Vitro PHA Synthesis by *Pseudomonas* Sp. SG4502-Derived PHA Synthase

SG 4502-derived PHA synthase I and PHA synthase II were isolated and prepared according to the following method to perform in vitro PHA synthesis.

(1) Isolation and Preparation of PHA Synthase I and PHA Synthase II

1) PHA Synthase I

Using pC1ZC2_SG4502 in the above Example 3 (4) as a template, PHA synthase I gene was amplified by PCR method under the following conditions, and a gene fragment (approx. 1.7 kbp) of the PHA synthase I, having BamHI site and KpnI site, was obtained. The gene fragment and a vector pQE80 (QIAGEN) digested with BamHI and KpnI were mixed to be ligated. Using a reaction solution, *Escherichia coli* JM109 was transformed. From a transformant obtained, a plasmid pQC 1SG having the PHA synthase I gene was obtained. By introducing the plasmid into an *Escherichia coli* BL21, *Escherichia coli* for preparing the PHA synthase I was prepared.

PCR condition:

Sense primer:
cgggatccaacaagatcgccgaagacctacag    (SEQ ID No: 10)

Anti sense primer:
ggggtacctcatcgttcgtgcacgtaggttcc    (SEQ ID No: 11)

Using Pyrobest DNA Polymerase (Takara), a reaction solution was prepared according to the manual. The PCR was performed in 30 cycles, each cycle comprising 20-second reaction at 98° C., 20-second reaction at 55° C. and 100-second reaction at 72° C.

2) PHA Synthase II

Using pC1ZC2_SG4502 as a template, PHA synthase II gene was amplified by PCR method under the following conditions, and a gene fragment (approx. 1.7 kbp) of the PHA synthase II, having BglII site and KpnI site, was obtained. The gene fragment and a vector pQE80 (QIAGEN) digested with BamHI and KpnI were mixed to be ligated. Using a reaction solution, *Escherichia coli* JM109 was transformed. From a transformant obtained, a plasmid pQC2SG having the PHA synthase II gene was obtained. By introducing the plasmid into an *Escherichia coli* BL21, *Escherichia coli* for preparing the PHA synthase II was prepared.

PCR condition on PHA synthase II gene:

Sense primer:
gaagatctcccacgcgccatcaaccgctgtc     (SEQ ID No: 12)

Antisense primer:
ggggtacctcagcgcaccagcacgtaggtgccc   (SEQ ID No: 13)

Using Pyrobest DNA Polymerase (Takara), a reaction solution was prepared according to the manual. The PCR was performed in 30 cycles, each cycle comprising 20-second reaction at 98° C., 20-second reaction at 65° C. and 100-second reaction at 72° C.

After *Escherichia coli* for preparing PHA synthase obtained in this Example (1) 1) and 2) were each cultured in 1000 mL of LB medium containing ampicillin at 20° C. for 8 hours, IPTG was added thereto so as to set its final concentration at 0.25 mM, and thereafter the product was cultured for another 16 hours to accumulate PHA synthase in a microbial cell body. After crushing the microbial cell body by the ultrasonic fragmentation, a soluble protein therein was collected. The collected protein was put into Ni-NTA agarose gel column (QIAGEN) to refine (6×His)-PHA synthase I or (6×His)-PHA synthase II in one step.

(2) PHA Production Test

Figure 8:
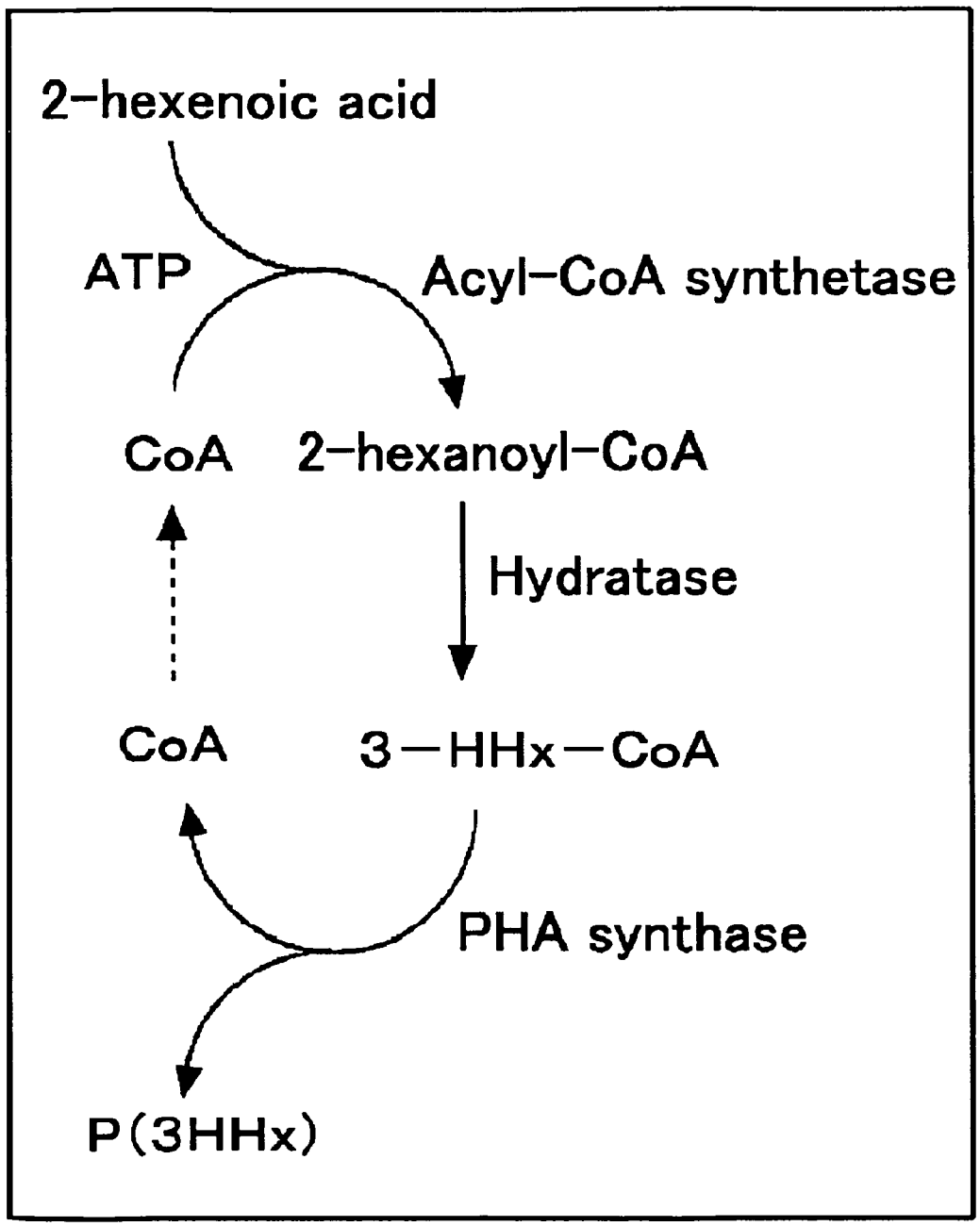
FIG. 8 is a diagram showing in vitro synthetic pathway of PHA in Example 4, using 2-hexenoic acid as a substrate.
Figure 9:
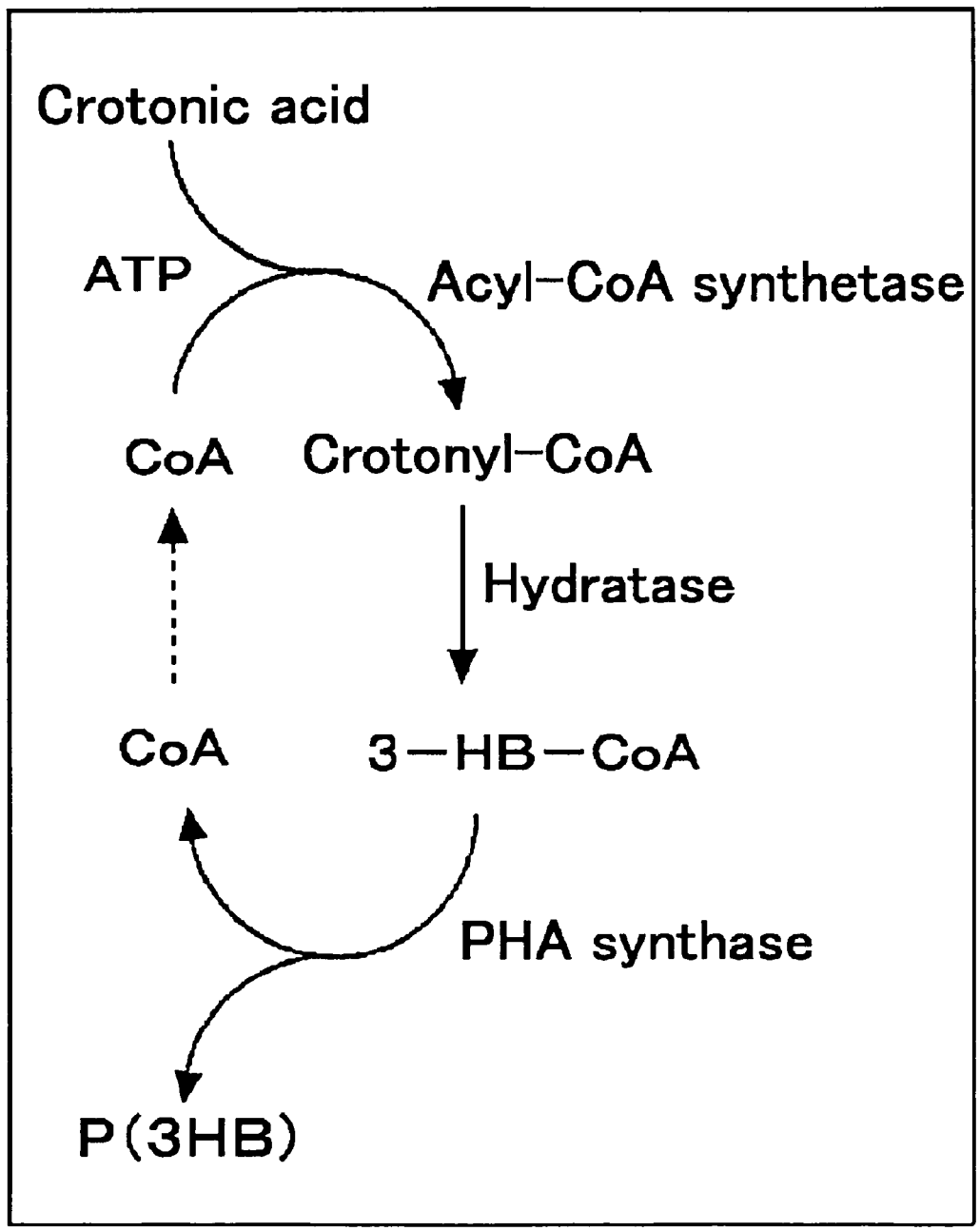
FIG. 9 is a diagram showing in vitro synthetic pathway of PHA in Example 4, using crotonic acid as a substrate.

Next, using the PHA synthase I and the PHA synthase II obtained in this Example (1), PHA was produced through a reaction pathway as shown in FIG. 8 or FIG. 9. Here, PHA production volume and other PHA properties were compared, using a plurality of substrates.

1) 2-Hexenoic Acid as a Substrate

Specifically, as an aqueous phase reaction solution, 5 mL of a solution, containing 100 mM Tris-HCl buffer (pH8.0), 11.0 mM CoA, 100 mM 2-hexenoic acid, 1.0 mg of acyl-CoA synthetase, 30 mM ATP, 10 mM $MgCl_2$, 0.2 mg/ml BSA, 0.4 U pyrophosphatase and hydratase, was prepared. Finally, 1.0 mg of PHA synthase I or PHA synthase II was added to an aqueous phase to be reacted at 30° C. for 72 hours. FIG. 8 shows the reaction pathway.

5 mL of chloroform was added to each reaction solution after the reaction was completed, and thereafter a product was extracted at 70° C. for 3 hours. After the product was filtrated with a filter (0.2 μm PTFE membrane; Advantec), 50 mL of methanol was added thereto and allowed to stand at 4° C. overnight. Afterward, a produced precipitate was filtrated with a filter (same as above) and collected. After each product was vacuum-dried, the yield thereof was measured. Consequently, 1.8 mg of a product by PHA synthase 1 and 2.4 mg of a product by PHA synthase II were obtained.

Figure 10:
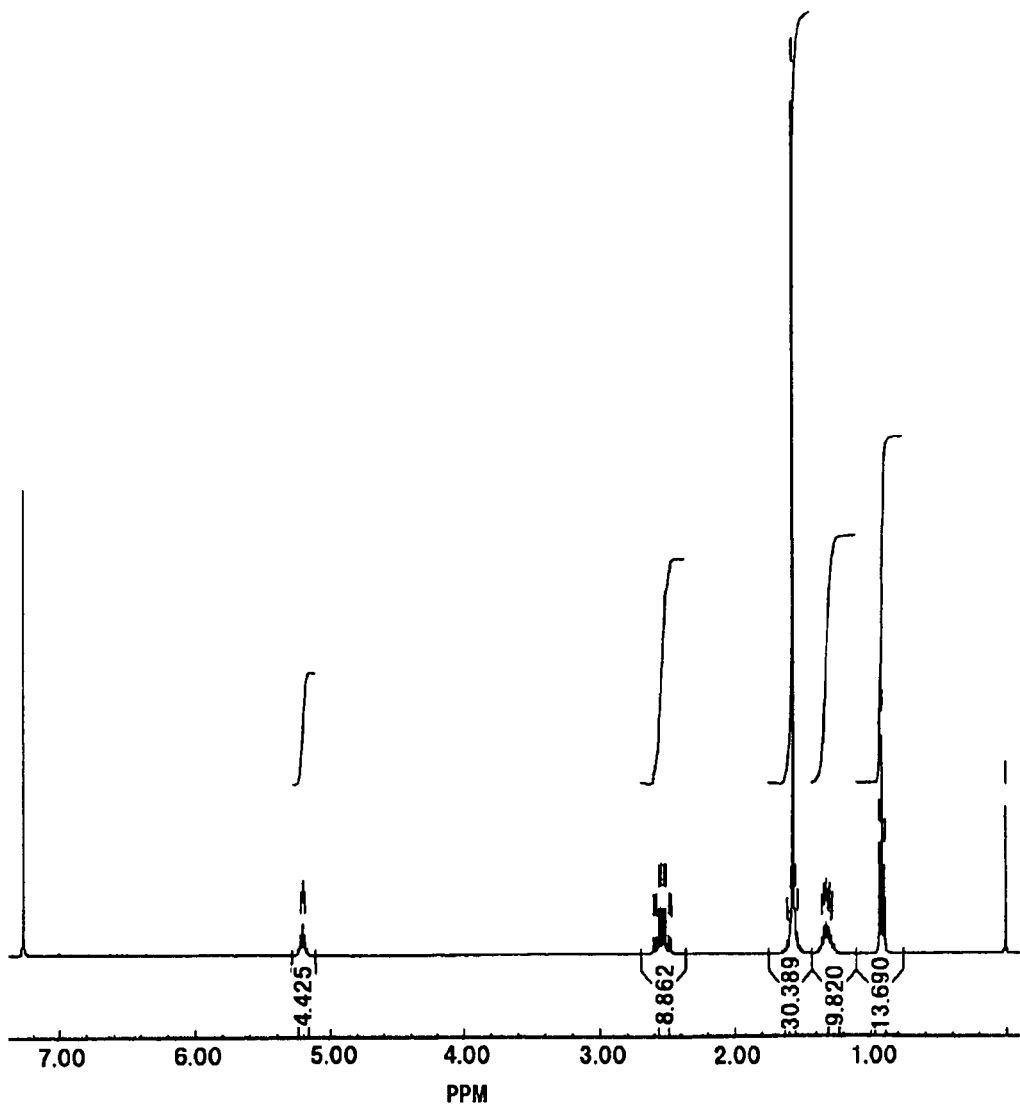
FIG. 10 is a diagram showing $^1$H-NMR spectrum of a compound produced in Example 4 (2), using PHA synthase I with 2-hexenoic acid as a substrate.
Figure 11:
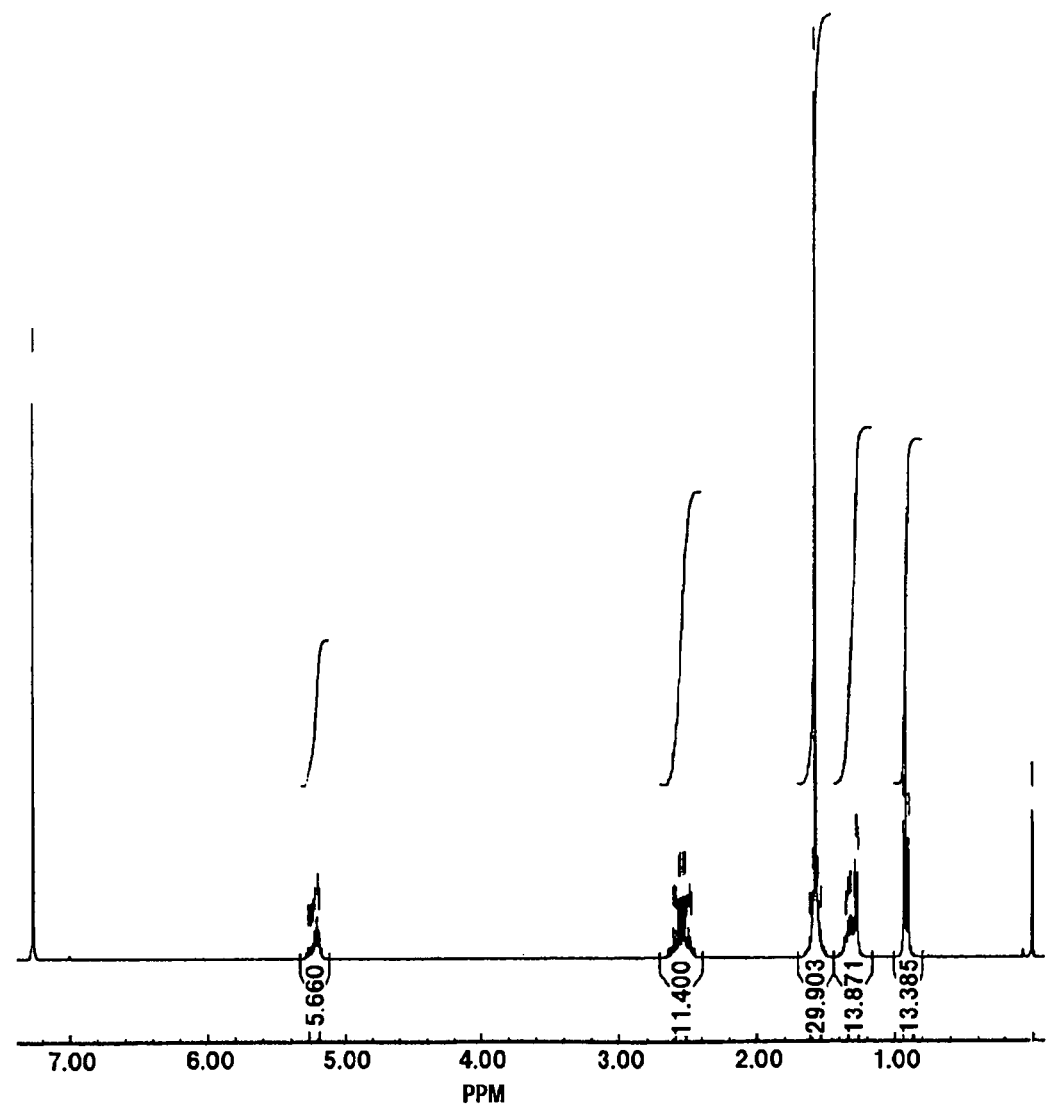
FIG. 11 is a diagram showing $^1$H-NMR spectrum of a compound produced in Example 4 (2), using PHA synthase II with 2-hexenoic acid as a substrate.

Next, the molecular structure of each product obtained was analyzed using NMR under the same conditions as in the above Example 2 (2). FIG. 10 shows $^1$H-NMR spectrum of a product obtained using PHA synthase I, and FIG. 11 shows $^1$H-NMR spectrum of a product obtained using PHA synthase II. As shown in the FIGS. 10 and 11, it was confirmed that both products are poly-3-hydroxyhexanoate {P (3HHx)}.

Subsequently, the molecular weight of each PHA obtained was measured by GPC under the same conditions as in the above Example 2 (3). As a result, in PHA obtained by PHA synthase I, $Mn=33.8\times10^4$, $Mw=72.6\times10^4$ and $Mn/Mw=1.7$. On the other hand, in PHA obtained by PHA synthase II, $Mn=17.1\times10^4$, $Mw=19.1\times10^4$ and $Mn/Mw=2.1$. These results demonstrate that the use of PHA synthase I or PHA synthase II can produce PHA of higher molecular weight.

2) Crotonic Acid as a Substrate

Figure 12:
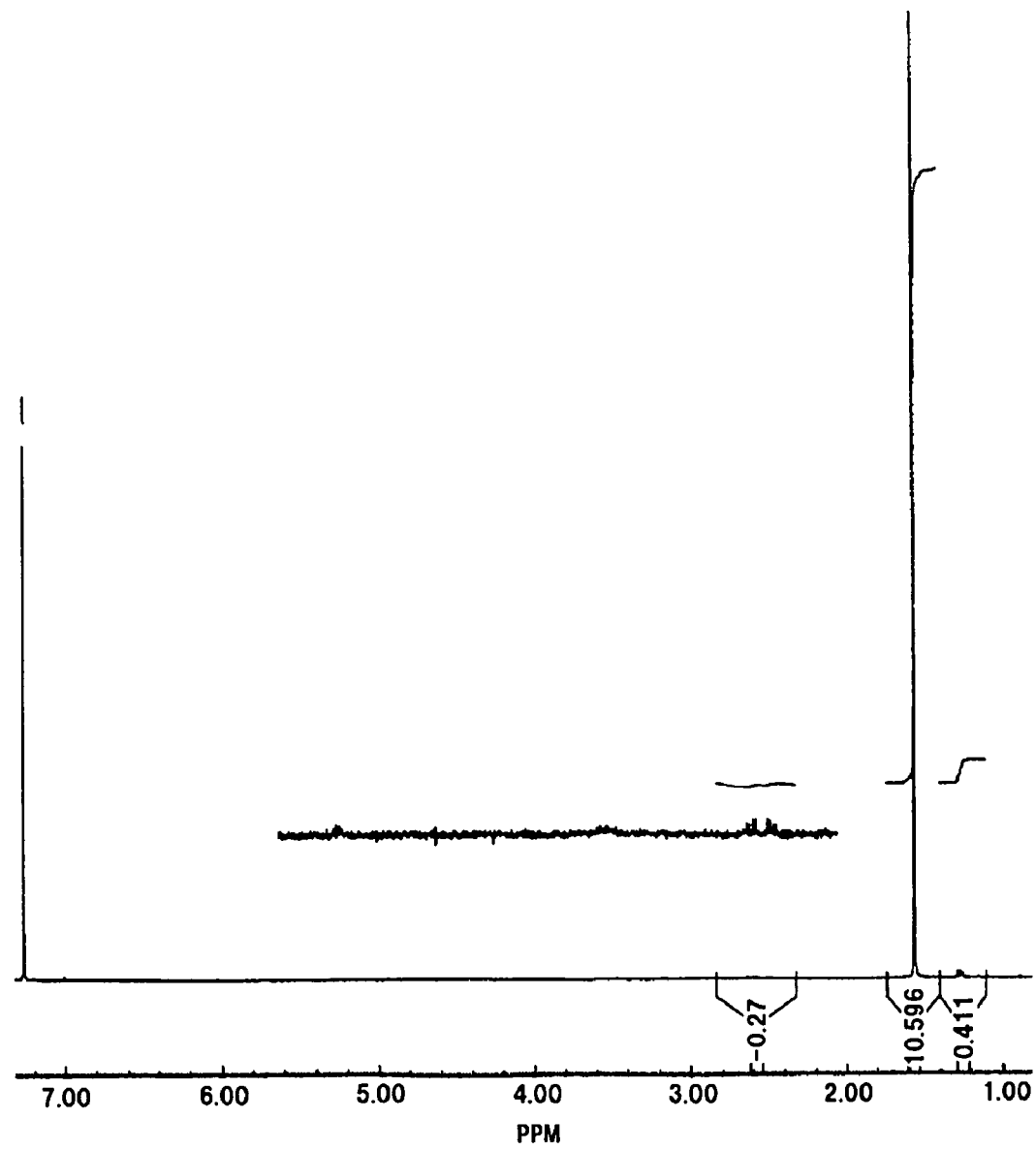
FIG. 12 is a diagram showing $^1$H-NMR spectrum of a compound produced in Example 4 (2), using PHA synthase II with crotonic acid as a substrate.

By substituting crotonic acid for the 2-hexenoic acid in the above 1), the same procedures were performed. FIG. 9 shows the reaction pathway. Consequently, the use of both PHA synthase I and PHA synthase II produced a PHA product. The PHA synthase II produced 0.3 mg of product, and its $^1$H-NMR spectrum (see FIG. 12) found that the product is poly-3-hydroxybutyrate {P(3HB)}.

Example 5

In Vivo PHA Synthesis Using *Pseudomonas* Sp. SG4502-Derived PHA Synthase Gene

Next, a transformant that is capable of producing a PHA by introducing SG4502-derived PHA synthase gene was prepared to produce PHA.

(1) Preparation of Transformant

First, using a chromosomal DNA of SG4502 obtained in the above Example 3 (1) as a template, a reaction solution was prepared according to the manual of KOD FX (TOYOBO). PHA synthase I gene and PHA synthase II gene were amplified by PCR under the following conditions.

PCR conditions:

```
PHA synthase I gene
Sense primer:
                                    (SEQ ID No: 14)
gccatgggca acaagatcgc cgaagaccta cagc Antisense primer:
                                    (SEQ ID No: 15)
tctagattca tcgttcgtgc acgtaggttc PHA synthase II gene
Sense primer:
                                    (SEQ ID No: 16)
ccatgggtcc cacgcgccat caaccgctg tcaac Antisense primer:
                                    (SEQ ID No: 17)
tgctctagat tcagcgcacc agcacgtagg
```

After one-cycle reaction for 2 minutes at 94° C. in PCR, another 30 cycles followed, each cycle comprising 10-second reaction at 94° C., 30-second reaction at 58° C. and 105-second reaction at 68° C.

Each amplified product was TA-cloned using TArget Clone-Plus-(TOYOBO), and plasmids obtained by PHA synthase I gene and PHA synthase II gene were defined as pTA-phaC1 sg and pTA-phaC2sg, respectively. Using these plasmids as a template, polynucleotide sequences of PHA synthase I gene and PHA synthase II gene were found by the method in the above Example 3 (3). Then, each plasmid was digested with restriction enzymes of NcoI and XbaI to obtain PHA synthase I gene and PHA synthase II gene.

Next, using a plasmid pTI305 (J. Biosci. Bioeng., v94, pp. 343-350, 2002) containing Ralstonia eutropha H16-derived synthase gene as a template, a reaction solution was prepared according to the manual of KOD-plus-(TOYOBO) to amplify an expression promoter region of PHA synthase gene by PCR under the following conditions. By this operation, a DNA fragment of gene expression promoter region having HindIII site was obtained.

PCR conditions:

```
Sense primer:
                                    (SEQ ID No: 18)
aaaccaagct tcccgggcaa gtaccttg Antisense primer:
                                    (SEQ ID No: 19)
aaccaagctt ccatggtttg attgtctctc tgc
```

After one-cycle reaction for 2 minutes at 94° C. in PCR, another 30 cycles followed, each cycle comprising 15-second reaction at 94° C., 30-second reaction at 55° C. and 60-second reaction at 68° C.

The DNA fragment and a cloning vector pUC18 (Takara) digested with a restriction enzyme of HindIII were mixed to be ligated, and a plasmid, in which the DNA fragment was inserted in a direction opposite to lac promoter of pUC18, was defined as pUC-Pre.

The plasmid pUC-Pre was digested with restriction enzymes of NcoI and XbaI. pUC-PrephaC1sg and pUC-PrephaC2sg were obtained, by inserting the PHA synthase I gene and the PHA synthase II gene, having NcoI site and XbaI site, into the plasmid pUC-Pre.

Using the pUC-PrephaC1sg, pUC-PrephaC2sg and pUC-Pre, each *Escherichia coli* BL21, having a plasmid pSRAB (J. Biosci. Bioeng., v94, pp. 343-350, 2002) containing Ralstonia eutropha H16-derived monomer synthesis-relating gene (β-ketothiolase gene and NADP-dependent acetoacetyl-CoA reductase gene), was transformed by a conventional method, thereby preparing pUC-PrephaC1sg transformant, pUC-PrephaC2sg transformant and pUC-Pre transformant.

(2) PHA Production Test

Subsequently, the pUC-PrephaC1sg transformant, the pUC-PrephaC2sg transformant and the pUC-Pre transformant prepared in this Example (1) were used to produce PHA.

Figure 13:
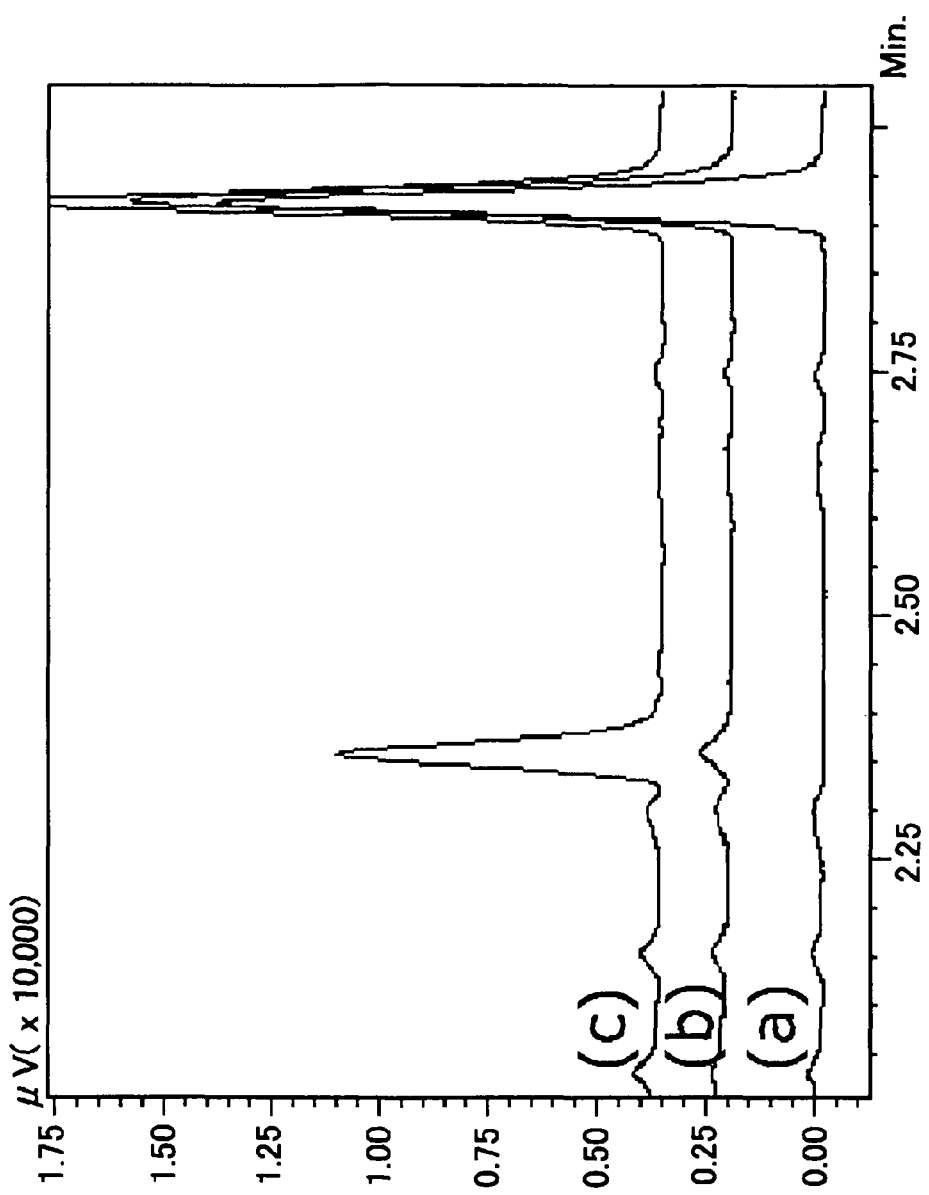
FIG. 13 is a diagram showing gas chromatography chart of a compound produced in Example 5 (2), using pUC-Pre transformant in (a), pUC-PrephaC1sg transformant in (b) and pUC-PrephaC2sg transformant in (c). In addition, the axis of ordinate of this figure shows detecting voltage and axis of abscissa of this figure shows retention time.

First, each transformant was inoculated into 2 mL of LB medium containing 100 μg/mL ampicillin and 30 μg/mL chloramphenicol, and the product was subjected to shaking culture at 37° C. overnight. The culture solution was all added to 500 mL baffle flask (IWAKI) containing 100 mL of LB medium having 1% glucose, 100 μg/mL ampicillin and 30 μg/mL chloramphenicol to be cultured at a speed of 160 rpm at 37° C. 8 hours after the culturing, IPTG was added thereto so as to set its final concentration at 0.5 mM, and thereafter the product was cultured for another 40 hours. After the culturing was completed, a microbial cell body was collected by centrifugal separation, washed with distilled water twice and lyophilized. Approx. 50 mg of the dry microbial cell body was treated with methanolysis according to a conventional method, and the product was analyzed by gas chromatograph method as in the above Example 2 (4). FIG. 13 shows the results of analysis in PHA production test, using pUC-Pre transformant in (a), pUC-PrephaC1sg transformant in (b) and pUC-PrephaC2sg transformant in (c).

Consequently, the PHA production test, using pUC-PrephaC1sg transformant and pUC-PrephaC2sg transformant, found that peak values derived from PHA, specifically P(3HB) were detected, as shown in FIG. 13 in (b) and (c). As shown in FIG. 13 in (a), however, the use of pUC-Pre transformant detected no PHA-derived peak value. From these observations, PHA synthase I and PHA synthase II are expressed by pUC-PrephaC1sg transformant and pUC-PrephaC2sg transformant, respectively, thereby polymerizing P (3HB).

According to the aforementioned embodiment, this invention can provide a new microorganism capable of producing a PHA, a PHA synthase gene, an expression cassette including the gene, a vector including the expression cassette, a transformant transformed by the vector, a polypeptide having PHA synthase activity, a method for producing a PHA synthase and a method for producing a PHA.

A new microorganism capable of producing a PHA, a PHA synthase gene, an expression cassette including the gene, a vector including the expression cassette, a transformant transformed by the vector, a polypeptide having PHA synthase activity, a method for producing a PHA synthase and a method for producing a PHA of this embodiment are not intended as a definition of the limits of the above description, but may be modified accordingly.

The invention claimed is:

1. An isolated microorganism of *Pseudomonas* sp. SG4502 as deposited at the National Institute of Technology and Evaluation and having an accession number NITE BP-578.

2. A method for producing a polyhydroxyalkanoate (PHA) synthase comprising:
   (a) culturing the microorganism of claim 1 in a medium, whereby a polyhydroxyalkanoate (PHA) synthase is produced in the medium, and
   (b) collecting the polyhydroxyalkanoate (PHA) synthase from the medium.

3. A method for producing a polyhydroxyalkanoate (PHA) comprising:
   (a) culturing the microorganism of claim 1 in a medium, whereby polyhydroxyalkanoate (PHA) is produced in the medium; and
   (b) collecting the polyhydroxyalkanoate (PHA) from the medium.

* * * * *

SEQUENCE LISTING

```
<160> NUMBER OF SEQ ID NOS: 19

<210> SEQ ID NO 1
<211> LENGTH: 527
<212> TYPE: DNA
<213> ORGANISM: Pseudomonas sp.

<400> SEQUENCE: 1
tggagagttt gatcctggct cagattgaac gctggcggca ggcctaacac atgcaagtcg       60
agcggcagca cgggagcttg ctcctggtgg cgagcggcgg acgggtgagt aatgcctagg      120
```

```
aatctgcctg ttagtggggg ataactcggg gaaactcgag ctaataccgc atacgtccta      180
cgggagaaag tggggacct tcgggcctca cgctaacaga tgagcctagg tcggattagc       240
tagttggtgg ggtaaaggcc taccaaggcg acgatccgta gctggtctga gaggatgatc      300
agccacactg gaactgagac acggtccaga ctcctacggg aggcagcagt ggggaatatt     360
ggacaatggg cgcaagcctg atccagccat gccgcgtgtg tgaagaaggt cttcggattg     420
taaagcactt taagttggga ggaagggctc ttggctaata cccgagggtt ttgacgttac     480
caacagaata agcaccggct aacttcgtgc cagcagccgc ggtaata                   527

<210> SEQ ID NO 2
<211> LENGTH: 1680
<212> TYPE: DNA
<213> ORGANISM: Pseudomonas sp.

<400> SEQUENCE: 2
atgaacaaga tcgccgaaga cctacagcgc caagcctcgg agcacaccct cagcctcaac      60
ccggtcgtgg gcctgcgcgg caaggatctc ctcagctcga cccgccaggt actcgtccag     120
gcgctgcgcc agcccctgca cagtacccgc acgtcgccc acttcggcgt gcagctgaag     180
aacgtcctgc tcggccaggc cgacctgaag ccggaggacg gcgaccgccg cttcgccgac     240
ccggcctgga gccacaatcc cctgtaccgc cgctacatgc agctctacct ggcctggcgc     300
caggagctgc acgactggat cgagcacagc aatctgccgc cccaggacat cagccgcggc     360
cacttcgtca tcaacctgct cactgaagca ctggcgccga gcaacagcct ggccaacccg     420
gcggccctca gcgcttcttt cgagaccggc ggcaagagcc tgctggacgg cctcgggcac     480
ctggccaagg acctggtgaa caatggcggc ctgcccagcc aggtgaacat ggaggccttc     540
gaggtgggca agaacctggc gctcaccgag ggcgccgtgg tgttccgcaa cgacctgcta     600
gagctgatcc agtaccggcc gaacaccgag caggtgcatg cccgaccact gctgatcgtc     660
ccgccgcaga tcaacaagtt ctacgtgttc gacctgtcgc cggacaagag cctggtgcga     720
ttcgccctgc gcagcggcct gcagaccttc atcctgagct ggcgcaaccc caccaagacc     780
cagcgcgaat ggggcctgtc cacctatatc gaggccctca aggaggccgt cgaggcggtt     840
ctggcgatca ccggcagcac cgacctgaac atgctcggcg cctgctccgg gggcatcacc     900
accgcggccc tgctcggcca ctacgcgccc gcggcgagc agccgatcca tgccctgacc     960
ctgctggtca gcgtgctgga taccgagatc gagacccagt tctcgctgtt cgtcgacgag    1020
cagactctgg aggccgccaa cgccgctccc taccaggccg gggtgctgga gggccgcaac    1080
ctggccaagc tgttcgcttg gatgcgcccc aacgacctga tctggaacta ctgggtcaac    1140
aactacctgc tcgggcgcca gccgccagcc ttcgacatcc tctactggaa caacgacacc    1200
acgcgcctgc cggccaccct gcacggcgac ctgatcgagc tgttcaagac caacccgctg    1260
ccccgcccgg gcgccctgga ggtgtgcggc acgcccatcg acctcaagca ggtcaagagc    1320
gacctctact gcgtggccgg ggtcaacgac cacatcactc cctgggaggc ctgctaccgc    1380
tcggcgcggc tgttcggggg cagcaccgag ttcgtgctgt ccaacagcgg gcacatccag    1440
gccatcctca acccgccggg caaccccaag gcgcgcttca tgaccggcaa cggcgagctc    1500
cccaccgagc ccaaggcctg gcaggagaac gccaccaagc agatcgactc ctggtggctg    1560
cactggcagg cctggctgac ggagcgctcc ggtccgctga agaaggcccc gggcaagctt    1620
ggcaacaagc agtacccgtc cggtgaagcg gccccggaa cctacgtgca cgaacgatga    1680

<210> SEQ ID NO 3
```

```
<211> LENGTH: 559
<212> TYPE: PRT
<213> ORGANISM: Pseudomonas sp.

<400> SEQUENCE: 3

Met Asn Lys Ile Ala Glu Asp Leu Gln Arg Gln Ala Ser Glu His Thr
1               5                   10                  15

Leu Ser Leu Asn Pro Val Val Gly Leu Arg Gly Lys Asp Leu Leu Ser
            20                  25                  30

Ser Thr Arg Gln Val Leu Val Gln Ala Leu Arg Gln Pro Leu His Ser
        35                  40                  45

Thr Arg His Val Ala His Phe Gly Val Gln Leu Lys Asn Val Leu Leu
    50                  55                  60

Gly Gln Ala Asp Leu Lys Pro Glu Asp Gly Asp Arg Arg Phe Ala Asp
65                  70                  75                  80

Pro Ala Trp Ser His Asn Pro Leu Tyr Arg Arg Tyr Met Gln Leu Tyr
                85                  90                  95

Leu Ala Trp Arg Gln Glu Leu His Asp Trp Ile Glu His Ser Asn Leu
            100                 105                 110

Pro Pro Gln Asp Ile Ser Arg Gly His Phe Val Ile Asn Leu Leu Thr
        115                 120                 125

Glu Ala Leu Ala Pro Ser Asn Ser Leu Ala Asn Pro Ala Ala Leu Lys
130                 135                 140

Arg Phe Phe Glu Thr Gly Gly Lys Ser Leu Leu Asp Gly Leu Gly His
145                 150                 155                 160

Leu Ala Lys Asp Leu Val Asn Asn Gly Gly Leu Pro Ser Gln Val Asn
                165                 170                 175

Met Glu Ala Phe Glu Val Gly Lys Asn Leu Ala Leu Thr Glu Gly Ala
            180                 185                 190

Val Val Phe Arg Asn Asp Leu Leu Glu Leu Ile Gln Tyr Arg Pro Asn
        195                 200                 205

Thr Glu Gln Val His Ala Arg Pro Leu Leu Ile Val Pro Pro Gln Ile
    210                 215                 220

Asn Lys Phe Tyr Val Phe Asp Leu Ser Pro Asp Lys Ser Leu Val Arg
225                 230                 235                 240

Phe Ala Leu Arg Ser Gly Leu Gln Thr Phe Ile Leu Ser Trp Arg Asn
                245                 250                 255

Pro Thr Lys Thr Gln Arg Glu Trp Gly Leu Ser Thr Tyr Ile Glu Ala
            260                 265                 270

Leu Lys Glu Ala Val Glu Ala Leu Ala Ile Thr Gly Ser Thr Asp
        275                 280                 285

Leu Asn Met Leu Gly Ala Cys Ser Gly Gly Ile Thr Thr Ala Ala Leu
    290                 295                 300

Leu Gly His Tyr Ala Ala Arg Gly Glu Gln Pro Ile His Ala Leu Thr
305                 310                 315                 320

Leu Leu Val Ser Val Leu Asp Thr Glu Ile Glu Thr Gln Phe Ser Leu
                325                 330                 335

Phe Val Asp Glu Gln Thr Leu Glu Ala Ala Lys Arg Arg Ser Tyr Gln
            340                 345                 350

Ala Gly Val Leu Glu Gly Arg Asn Leu Ala Lys Leu Phe Ala Trp Met
        355                 360                 365

Arg Pro Asn Asp Leu Ile Trp Asn Tyr Trp Val Asn Tyr Leu Leu
    370                 375                 380

Gly Arg Gln Pro Pro Ala Phe Asp Ile Leu Tyr Trp Asn Asn Asp Thr
385                 390                 395                 400
```

```
Thr Arg Leu Pro Ala Thr Leu His Gly Asp Leu Ile Glu Leu Phe Lys
            405                 410                 415

Thr Asn Pro Leu Pro Arg Pro Gly Ala Leu Glu Val Cys Gly Thr Pro
        420                 425                 430

Ile Asp Leu Lys Gln Val Lys Ser Asp Leu Tyr Cys Val Ala Gly Val
            435                 440                 445

Asn Asp His Ile Thr Pro Trp Glu Ala Cys Tyr Arg Ser Ala Arg Leu
450                 455                 460

Phe Gly Gly Ser Thr Glu Phe Val Leu Ser Asn Ser Gly His Ile Gln
465                 470                 475                 480

Ala Ile Leu Asn Pro Pro Gly Asn Pro Lys Ala Arg Phe Met Thr Gly
                485                 490                 495

Asn Gly Glu Leu Pro Thr Glu Pro Lys Ala Trp Gln Glu Asn Ala Thr
            500                 505                 510

Lys Gln Ile Asp Ser Trp Trp Leu His Trp Gln Ala Trp Leu Thr Glu
        515                 520                 525

Arg Ser Gly Pro Leu Lys Lys Ala Pro Gly Lys Leu Gly Asn Lys Gln
    530                 535                 540

Tyr Pro Ser Gly Glu Ala Ala Pro Gly Thr Tyr Val His Glu Arg
545                 550                 555
```

<210> SEQ ID NO 4
<211> LENGTH: 1692
<212> TYPE: DNA
<213> ORGANISM: Pseudomonas sp.

<400> SEQUENCE: 4

```
atgcccacgc gccatcaacc cgctgtcaac accctgccag ctcccgctgc cttcatgaat      60
gcccagaacg ccgtggtcgg cctgcgcggc cgcgacctgc tctccagcgc tcgcgacatc     120
gccctgcacg ggctcagaca cccgctgcac ggcacccgac acctgctgtc cttcggcaaa     180
cagctgggcc gggtactgct cggcgacacc ctgtatgcgc ccaaccccgg cgacgtccgt     240
ttcgccgatc ccacctggca gctcaatccg ctctaccggc gcggactgca ggcctacctg     300
gcctggcaga agcagctcgt ccagtggatc gacgagagcg acctgagcgc cgacgaccgc     360
acccgcgcgc tgttcctcgc ctcgctgctc agcgacgccc tggcgccgtc aacagccta     420
ctcaacccgc tggccatcaa agagctgttc gacaccggcg gcggcagcct gctgcgcggc     480
ctgcgccacc tgatcgacga cctgctgcac aacgacggtc tgcccagcca ggtcaacaag     540
caggccttcg aggtcggcaa gaacctggcc accaccccg gctcggtggt gttccgcaac     600
gagatgctgg agctgatcca gtaccggccg atgagcgaga agcagtacga acggccgctg     660
ctgatcgtcc gccgcagat caacaagttc tacatcttcg acctgagccc ggagaagagc     720
ttcgtccagt acgccctgaa gaacgacctg caggtgttca tgatcagctg gcgcaacccc     780
gacgcgcggc accgcgaatg gggcctgtcc agctacgtgc aggccctcga cgaggcgctg     840
gaggtgtgcc gggcgatcac cggcagcaag gcggtcaacc tgctcggcgc ctgcgccggc     900
ggcctcaccg cggcggcgct gatgggccac ctgcaggcgc cggcagct cgcaagatc       960
gccagcgcca gctatgcggt gagcctcttg gacagccaga tcgaaagcag cccggcgctg    1020
ctgttcgtcg acgagcagac cctggaggcc gccaagcgcc gctcctacca ggccggggtg    1080
ctggacggcc gcgacctggc caaggtgttc gcctggatgc gccccaacga cctgatctgg    1140
aactactggg tcaacaacta cctgctcggg cgccagccgc cggccttcga catcctctac    1200
tggaacaacg acaacacccg cctgccggct gccctgcacg gcgacctgct ggacatcttc    1260
```

| aagcacaacc cgctgacccg ccccggcggc ctggaagtgt gcggcacgcc catcgacctg | 1320 |
| cagagggtca ccgtggacag cttctgcgtg gccggcatca acgaccacat cacccccgg | 1380 |
| gacgcggtgt accgctcgct gctgctgctc ggcggcgaac ggcgcttcat cctctccaac | 1440 |
| gccggacaca tccaggccat cctcaacccg ccgggcaacc ccaaggccca ctacttcgag | 1500 |
| aacggcaggc tgagcgccga cccgcgcgcc tggtactacg acgcgcggaa ggtggagggc | 1560 |
| agctggtggc cggagtggct ggcctggatc caggcccgct ccggcgagca gcggccgacc | 1620 |
| cggatgagca tcggcaacgc ccgctacccg gccctggagg cggcgccggg cacctacgtg | 1680 |
| ctggtgcgct ga | 1692 |

<210> SEQ ID NO 5
<211> LENGTH: 563
<212> TYPE: PRT
<213> ORGANISM: Pseudomonas sp.

<400> SEQUENCE: 5

Met Pro Thr Arg His Gln Pro Ala Val Asn Thr Leu Pro Ala Pro Ala
1               5                   10                  15

Ala Phe Met Asn Ala Gln Asn Ala Val Val Gly Leu Arg Gly Arg Asp
            20                  25                  30

Leu Leu Ser Ser Ala Arg Asp Ile Ala Leu His Gly Leu Arg His Pro
        35                  40                  45

Leu His Gly Thr Arg His Leu Leu Ser Phe Gly Lys Gln Leu Gly Arg
    50                  55                  60

Val Leu Leu Gly Asp Thr Leu Tyr Ala Pro Asn Pro Gly Asp Val Arg
65                  70                  75                  80

Phe Ala Asp Pro Thr Trp Gln Leu Asn Pro Leu Tyr Arg Arg Gly Leu
                85                  90                  95

Gln Ala Tyr Leu Ala Trp Gln Lys Gln Leu Val Gln Trp Ile Asp Glu
            100                 105                 110

Ser Asp Leu Ser Ala Asp Arg Thr Arg Ala Leu Phe Leu Ala Ser
        115                 120                 125

Leu Leu Ser Asp Ala Leu Ala Pro Ser Asn Ser Leu Leu Asn Pro Leu
    130                 135                 140

Ala Ile Lys Glu Leu Phe Asp Thr Gly Gly Ser Leu Leu Arg Gly
145                 150                 155                 160

Leu Arg His Leu Ile Asp Asp Leu Leu His Asn Asp Gly Leu Pro Ser
                165                 170                 175

Gln Val Asn Lys Gln Ala Phe Glu Val Gly Lys Asn Leu Ala Thr Thr
            180                 185                 190

Pro Gly Ser Val Val Phe Arg Asn Glu Met Leu Glu Leu Ile Gln Tyr
        195                 200                 205

Arg Pro Met Ser Glu Lys Gln Tyr Glu Arg Pro Leu Leu Ile Val Pro
    210                 215                 220

Pro Gln Ile Asn Lys Phe Tyr Ile Phe Asp Leu Ser Pro Glu Lys Ser
225                 230                 235                 240

Phe Val Gln Tyr Ala Leu Lys Asn Asp Leu Gln Val Phe Met Ile Ser
                245                 250                 255

Trp Arg Asn Pro Asp Ala Arg His Arg Glu Trp Gly Leu Ser Ser Tyr
            260                 265                 270

Val Gln Ala Leu Asp Glu Ala Leu Glu Val Cys Arg Ala Ile Thr Gly
        275                 280                 285

Ser Lys Ala Val Asn Leu Leu Gly Ala Cys Ala Gly Gly Leu Thr Ala

```
                     290                 295                 300
Ala Ala Leu Met Gly His Leu Gln Ala Arg Arg Gln Leu Arg Lys Ile
305                 310                 315                 320

Ala Ser Ala Ser Tyr Ala Val Ser Leu Leu Asp Ser Gln Ile Glu Ser
                325                 330                 335

Ser Pro Ala Leu Leu Phe Val Asp Glu Gln Thr Leu Glu Ala Ala Lys
                340                 345                 350

Arg Arg Ser Tyr Gln Ala Gly Val Leu Asp Gly Arg Asp Leu Ala Lys
                355                 360                 365

Val Phe Ala Trp Met Arg Pro Asn Asp Leu Ile Trp Asn Tyr Trp Val
370                 375                 380

Asn Asn Tyr Leu Leu Gly Arg Gln Pro Pro Ala Phe Asp Ile Leu Tyr
385                 390                 395                 400

Trp Asn Asn Asp Asn Thr Arg Leu Pro Ala Ala Leu His Gly Asp Leu
                405                 410                 415

Leu Asp Ile Phe Lys His Asn Pro Leu Thr Arg Pro Gly Gly Leu Glu
                420                 425                 430

Val Cys Gly Thr Pro Ile Asp Leu Gln Arg Val Thr Val Asp Ser Phe
                435                 440                 445

Cys Val Ala Gly Ile Asn Asp His Ile Thr Pro Trp Asp Ala Val Tyr
                450                 455                 460

Arg Ser Leu Leu Leu Leu Gly Gly Glu Arg Phe Ile Leu Ser Asn
465                 470                 475                 480

Ala Gly His Ile Gln Ala Ile Leu Asn Pro Pro Gly Asn Pro Lys Ala
                485                 490                 495

His Tyr Phe Glu Asn Gly Arg Leu Ser Ala Asp Pro Arg Ala Trp Tyr
                500                 505                 510

Tyr Asp Ala Arg Lys Val Glu Gly Ser Trp Trp Pro Glu Trp Leu Ala
                515                 520                 525

Trp Ile Gln Ala Arg Ser Gly Glu Gln Arg Pro Thr Arg Met Ser Ile
                530                 535                 540

Gly Asn Ala Arg Tyr Pro Ala Leu Glu Ala Ala Pro Gly Thr Tyr Val
545                 550                 555                 560

Leu Val Arg

<210> SEQ ID NO 6
<211> LENGTH: 906
<212> TYPE: DNA
<213> ORGANISM: Pseudomonas sp.

<400> SEQUENCE: 6
atgaagagcg ttcctcccgc cccggcgccg gacggcaccg ccagcccgcc cagccccttc      60
gtgttccgca ccatcgagct ggacggccag accctgcgca ccgcggtgcg tcccggcagc     120
tcgccgctgc ccccgctgct gatctgcaac ggcataggcg ccaacctgga gctggtgctg     180
cccttcgtcc aggccctcga tccggacctc gaggtgatcg ccttcgacgt gcccggcgtg     240
ggcggctcct ccacgcccag cctgccctac cgcttccccg gcctggccag gctgatcgcg     300
cggatgctcg actacctgga ctacggccag gtcaacgtga tcggcgtgtc ttggggcggc     360
gccctggccc agcagttcgc ccacgacttc cggagcgct gcaagaagct ggtgctcgcc     420
gctacctcgg ccggcgcggt gatggttccc ggcaagccca gggtgctctg cgcatggcc     480 agtccgcggc gctacctcca gccatcctac ggggtacgca tcgccccgga catctacggc     540
ggcgccttcc gccgcgacgc cagcctggcc ctcagccacg ccagcaaggt gcgctccggc     600
```

-continued

```
ggcaagctgg gctactactg gcagctgttc gccggcctgg gctggaccag cttccactgg    660
ctgcaccgga tccgccagcc gaccctggtg ctggccggcg acgacgaccc catcatcccg    720
ctgatcaaca tgcgcatgct cgcctggcgg atccccaacg ccgagctgca cgtgatcgac    780
gacggccacc tgttcctgat cacccgcgcc gaggcggtgg cgccgctgat catgaagttc    840
cttgaggagg agaagcagcg cgcggtgatg cacccgcacc ctgccccggg cgggcgcaca    900
tcctga                                                                906
```

<210> SEQ ID NO 7
<211> LENGTH: 301
<212> TYPE: PRT
<213> ORGANISM: Pseudomonas sp.

<400> SEQUENCE: 7

```
Met Lys Ser Val Pro Ala Pro Ala Pro Asp Gly Thr Ala Ser Pro
 1               5                  10                  15

Pro Ser Pro Phe Val Phe Arg Thr Ile Glu Leu Asp Gly Gln Thr Leu
                20                  25                  30

Arg Thr Ala Val Arg Pro Gly Ser Ser Pro Leu Pro Pro Leu Leu Ile
                35                  40                  45

Cys Asn Gly Ile Gly Ala Asn Leu Glu Leu Val Leu Pro Phe Val Gln
    50                  55                  60

Ala Leu Asp Pro Asp Leu Glu Val Ile Ala Phe Asp Val Pro Gly Val
65                  70                  75                  80

Gly Gly Ser Ser Thr Pro Ser Leu Pro Tyr Arg Phe Pro Gly Leu Ala
                85                  90                  95

Arg Leu Ile Ala Arg Met Leu Asp Tyr Leu Asp Tyr Gly Gln Val Asn
                100                 105                 110

Val Ile Gly Val Ser Trp Gly Gly Ala Leu Ala Gln Gln Phe Ala His
            115                 120                 125

Asp Phe Pro Glu Arg Cys Lys Lys Leu Val Leu Ala Ala Thr Ser Ala
    130                 135                 140

Gly Ala Val Met Val Pro Gly Lys Pro Arg Val Leu Trp Arg Met Ala
145                 150                 155                 160

Ser Pro Arg Arg Tyr Leu Gln Pro Ser Tyr Gly Val Arg Ile Ala Pro
                165                 170                 175

Asp Ile Tyr Gly Gly Ala Phe Arg Arg Asp Ala Ser Leu Ala Leu Ser
                180                 185                 190

His Ala Ser Lys Val Arg Ser Gly Gly Lys Leu Gly Tyr Tyr Trp Gln
            195                 200                 205

Leu Phe Ala Gly Leu Gly Trp Thr Ser Phe His Trp Leu His Arg Ile
    210                 215                 220

Arg Gln Pro Thr Leu Val Leu Ala Gly Asp Asp Pro Ile Ile Pro
225                 230                 235                 240

Leu Ile Asn Met Arg Met Leu Ala Trp Arg Ile Pro Asn Ala Glu Leu
                245                 250                 255

His Val Ile Asp Asp Gly His Leu Phe Leu Ile Thr Arg Ala Glu Ala
                260                 265                 270

Val Ala Pro Leu Ile Met Lys Phe Leu Glu Glu Glu Lys Gln Arg Ala
            275                 280                 285

Val Met His Pro His Pro Ala Pro Gly Gly Arg Thr Ser
    290                 295                 300
```

<210> SEQ ID NO 8
<211> LENGTH: 24

```
<212> TYPE: DNA
<213> ORGANISM: Artificial
<220> FEATURE:
<223> OTHER INFORMATION: FW primer

<400> SEQUENCE: 8
ccatgacagc ggcctgttca cctg                                              24

<210> SEQ ID NO 9
<211> LENGTH: 25
<212> TYPE: DNA
<213> ORGANISM: Artificial
<220> FEATURE:
<223> OTHER INFORMATION: RV primer

<400> SEQUENCE: 9
tcgacgatca ggtgcaggaa cagcc                                             25

<210> SEQ ID NO 10
<211> LENGTH: 32
<212> TYPE: DNA
<213> ORGANISM: Artificial
<220> FEATURE:
<223> OTHER INFORMATION: sense primer

<400> SEQUENCE: 10
cgggatccaa caagatcgcc gaagacctac ag                                     32

<210> SEQ ID NO 11
<211> LENGTH: 32
<212> TYPE: DNA
<213> ORGANISM: Artificial
<220> FEATURE:
<223> OTHER INFORMATION: antisence primer

<400> SEQUENCE: 11
ggggtacctc atcgttcgtg cacgtaggtt cc                                     32

<210> SEQ ID NO 12
<211> LENGTH: 32
<212> TYPE: DNA
<213> ORGANISM: Artificial
<220> FEATURE:
<223> OTHER INFORMATION: sence primer

<400> SEQUENCE: 12
gaagatctcc cacgcgccat caacccgctg tc                                     32

<210> SEQ ID NO 13
<211> LENGTH: 33
<212> TYPE: DNA
<213> ORGANISM: sense primer

<400> SEQUENCE: 13
ggggtacctc agcgcaccag cacgtaggtg ccc                                    33

<210> SEQ ID NO 14
<211> LENGTH: 34
<212> TYPE: DNA
<213> ORGANISM: Artificial
<220> FEATURE:
<223> OTHER INFORMATION: sense primer

<400> SEQUENCE: 14
gccatgggca acaagatcgc cgaagaccta cagc                                   34
```

```
<210> SEQ ID NO 15
<211> LENGTH: 30
<212> TYPE: DNA
<213> ORGANISM: anrisense primer

<400> SEQUENCE: 15
tctagattca tcgttcgtgc acgtaggttc                                    30

<210> SEQ ID NO 16
<211> LENGTH: 35
<212> TYPE: DNA
<213> ORGANISM: Artificial
<220> FEATURE:
<223> OTHER INFORMATION: sense primer

<400> SEQUENCE: 16
ccatgggtcc cacgcgccat caacccgctg tcaac                              35

<210> SEQ ID NO 17
<211> LENGTH: 30
<212> TYPE: DNA
<213> ORGANISM: Artificial
<220> FEATURE:
<223> OTHER INFORMATION: antisense primer

<400> SEQUENCE: 17
tgctctagat tcagcgcacc agcacgtagg                                    30

<210> SEQ ID NO 18
<211> LENGTH: 28
<212> TYPE: DNA
<213> ORGANISM: Artificial
<220> FEATURE:
<223> OTHER INFORMATION: sense primer

<400> SEQUENCE: 18
aaaccaagct tcccgggcaa gtaccttg                                      28

<210> SEQ ID NO 19
<211> LENGTH: 33
<212> TYPE: DNA
<213> ORGANISM: Artificial
<220> FEATURE:
<223> OTHER INFORMATION: antisense primer

<400> SEQUENCE: 19
aaccaagctt ccatggtttg attgtctctc tgc                                33
```